United States Patent
Rezania

(10) Patent No.: US 10,947,511 B2
(45) Date of Patent: Mar. 16, 2021

(54) DIFFERENTIATION OF HUMAN EMBRYONIC STEM CELLS INTO PANCREATIC ENDOCRINE CELLS USING THYROID HORMONE AND/OR ALK5, AN INHIBITOR OF TGF-BETA TYPE 1 RECEPTOR

(71) Applicant: Janssen Biotech, Inc., Horsham, PA (US)

(72) Inventor: Alireza Rezania, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 102 days.

(21) Appl. No.: 16/200,469

(22) Filed: Nov. 26, 2018

(65) Prior Publication Data
US 2019/0211309 A1 Jul. 11, 2019

Related U.S. Application Data

(62) Division of application No. 13/998,883, filed on Dec. 18, 2013, now Pat. No. 10,138,465.

(60) Provisional application No. 61/747,672, filed on Dec. 31, 2012.

(51) Int. Cl.
*C12N 5/071* (2010.01)
*C12N 5/0735* (2010.01)

(52) U.S. Cl.
CPC ......... *C12N 5/0676* (2013.01); *C12N 5/0606* (2013.01); *C12N 2501/117* (2013.01); *C12N 2501/15* (2013.01); *C12N 2501/16* (2013.01); *C12N 2501/19* (2013.01); *C12N 2501/395* (2013.01); *C12N 2501/415* (2013.01); *C12N 2501/727* (2013.01); *C12N 2501/999* (2013.01); *C12N 2506/02* (2013.01); *C12N 2533/90* (2013.01)

(58) Field of Classification Search
CPC .................................................. C12N 5/0676
See application file for complete search history.

(56) References Cited

U.S. PATENT DOCUMENTS

| | | | |
|---|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |

(Continued)

FOREIGN PATENT DOCUMENTS

| CN | 1389565 A | 7/2002 |
|---|---|---|
| CN | 1602351 A | 3/2005 |

(Continued)

OTHER PUBLICATIONS

Abe, et al., Evidence That P13K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

Ackermann, et al., Molecular Regulation of Pancreatic B-Cell Mass Development, Maintenance, and Expansion, Journal of Molecular Endocrinology, 2007, pp. 193-206, vol. 38.

(Continued)

*Primary Examiner* — Thainan N. Ton
*Assistant Examiner* — David A. Montanari
(74) *Attorney, Agent, or Firm* — Klarquist Sparkman, LLP

(57) ABSTRACT

The present invention provides methods to promote differentiation of pluripotent stem cells to pancreatic endoderm cells expressing PDX1, NKX6.1, and HB9. In particular, the methods encompass culturing Stage 4 to Stage 6 cells with a thyroid hormone (e.g. T3), an ALK5 inhibitor, or both.

12 Claims, 17 Drawing Sheets

(56) References Cited

U.S. PATENT DOCUMENTS

| | | |
|---|---|---|
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 9,528,090 B2 | 12/2016 | Rezania |
| 10,138,465 B2 * | 11/2018 | Rezania ............... C12N 5/0676 |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2012/0045830 A1 | 2/2012 | Green et al. |
| 2012/0190111 A1 | 7/2012 | Davis et al. |
| 2013/0189777 A1 | 7/2013 | Rezania |
| 2013/0224156 A1 | 8/2013 | Takahashi et al. |
| 2014/0186953 A1 | 7/2014 | Rezania |
| 2014/0329704 A1 | 11/2014 | Melton et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2604685 A4 | 3/2014 |
| EP | 2479260 B1 | 6/2016 |
| GB | 2484873 B2 | 4/2014 |
| JP | 2005506074 A2 | 3/2003 |
| JP | 2005537803 A1 | 12/2005 |
| JP | 2006-500003 A2 | 1/2006 |
| JP | 2008500809 A2 | 1/2008 |
| JP | 2009513143 A2 | 4/2009 |

(56) References Cited

FOREIGN PATENT DOCUMENTS

| | | |
|---|---|---|
| KR | 10-2008-0020098 A | 3/2008 |
| RU | 1767433 A1 | 10/1992 |
| RU | 2359030 C1 | 6/2009 |
| RU | 2359671 C2 | 6/2009 |
| WO | 199219759 A2 | 2/1992 |
| WO | 1996040172 A1 | 12/1996 |
| WO | 98/30679 A1 | 7/1998 |
| WO | 199847892 A1 | 10/1998 |
| WO | 199920741 A1 | 4/1999 |
| WO | 200029549 A1 | 5/2000 |
| WO | 200123528 A1 | 4/2001 |
| WO | 200151616 A2 | 7/2001 |
| WO | 200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | 200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | 2003102134 A2 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | 2004090110 A2 | 10/2004 |
| WO | 2004067001 A1 | 12/2004 |
| WO | 2005001077 A2 | 1/2005 |
| WO | 2005080598 A1 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006088867 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007027157 A1 | 3/2007 |
| WO | 2007030870 A1 | 3/2007 |
| WO | 2007047509 A1 | 4/2007 |
| WO | 2007051038 A2 | 5/2007 |
| WO | 2007069666 A1 | 6/2007 |
| WO | 2007082963 A1 | 7/2007 |
| WO | 2007101130 A2 | 9/2007 |
| WO | 2007103282 A1 | 9/2007 |
| WO | 2007127927 A2 | 11/2007 |
| WO | 2007136673 A2 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2009096049 A1 | 5/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009048675 A1 | 4/2009 |
| WO | 2009061442 A1 | 5/2009 |
| WO | 2009070592 A1 | 6/2009 |
| WO | 2009090424 A1 | 7/2009 |
| WO | 2009096902 A1 | 8/2009 |
| WO | 2009101407 A2 | 8/2009 |
| WO | 2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011096223 A1 | 8/2011 |
| WO | 2011108993 A1 | 9/2011 |
| WO | 2011160066 A1 | 12/2011 |
| WO | 2012019122 A2 | 2/2012 |
| WO | 2012117333 A1 | 9/2012 |
| WO | 2013055397 A1 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2015002724 A4 | 3/2015 |

OTHER PUBLICATIONS

Adams, J., Proteasome Inhibition in Cancer: Development of PS-341, Seminars in Oncology, 2001, pp. 613-619, vol. 28, No. 6.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit et al., Human Feeder Layers for Human Embryonic Stem Cells, Biology of Reproduction, Jan. 22, 2003, 2150-2156, 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Feeder Layer-and Serum-Free Culture of Human Embryonic Stem Cells, Biology of Reproduction, 2004, pp. 837-845, vol. 70.

(56) References Cited

OTHER PUBLICATIONS

Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . . , Blood, Jun. 1, 1997, 3960-3966, 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature Biotechnology, Apr. 1, 2004, 381-382, 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesencymal Stem Cells in Pancreatic Islet Beta-Cells, World Journal of Gastroenterology, Oct. 15, 2004, pp. 3016-3020.
Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.
Cheon, et al., Defined Feeder-Free Culture System of Human Embryonic Stem Cells, Biol Reprod, 2005, 105.046870, DOI10/1095.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Efficient differentiation of human embryonic stem cells to definitive endoderm, Nature Biotechnology, Oct. 28, 2005, 1-8, :W.1038/nbt1163, Nature Publishing Group.
D'Amour et al., Production of pancreatic hormone-expressing endocrine cells from human embryonic stem cells, Nature Biotechnology, Oct. 19, 2006, 1392-1401, 24-11, Nature Publishing Group, US.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat,

(56) References Cited

OTHER PUBLICATIONS

Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

De Rosa, 11-color, 13-parameter flow cytometry: Identification of . . . , Nature, Feb. 1, 2001, 245-248, 7-2, Nature Publishing Group, US.

Dekker, et al., Adhesion of Endothelial Cells and Adsorption of Serum Proteins on Gas Plasma-Treated Polytetrafluoroethylene, Biomaterials, 1991, pp. 130-138, vol. 12.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Recurrent Gain of Chromosomes 17q and 12 in Cultured Human Embryonic Stem Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dufour, et al., Development of an Ectopic Site for Islet Transplantation Using Biodegradable Scaffolds, Tissue Engineering, 2005, pp. 1323-1331 XP002699177, vol. 11, No. 9/10.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Ellerstrom, et al., Derivation of a Xeno-Free Human Embryonic Stem Cell Line, Stem Cells, 2006, pp. 2170-2176, vol. 24.

Ellerstrom, et al., Facilitated Expansion of Human Embryonic Stem Cells by Single-Cell Enzymatic Dissociation, Stem Cells, 2007, pp. 1690-1696, vol. 25, No. 7.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Enzmann, et al., Enhanced Induction of RPE Lineage Markers in Pluripootent Neural Stem Cells Engrafted into the Adult Rat Subretinal Space, Investigative Ophthamology & Visual Science, Dec. 2003, pp. 5417-5422, vol. 44, No. 12, Association for Research in Vision and Ophthamology.

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low O2 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, 727-732, 137-2, American Society of Immunologists, US.

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

Fok, et al., Shear-Controlled Single-Step Mouse Embryonic Stem Cell Expansion and Embryoid Body-Based Differentiation, Stem Cells, 2005, pp. 1333-1342, vol. 23.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.

Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.

Gershengorn et al., Epithelial-to-Mesenchymal Transition Generates Proliferative Human Islet Precursor Cells, Science, Dec. 24, 2004, 2261-2264, 306, US.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.

Gittest, Developmental Biology of the Pancreas: A comprehensive Review, Developmental Biology, 2009, pp. 4-35 XP025995041, vol. 326, No. 1.

Gosden, et al., Amniotic Fluid Cell Types and Culture, British Medical Bulletin, 1983, pp. 348-354, vol. 39, No. 4.

Graham, et al., Characteristics of a Human Cell Line Transformed by DNA from Human Adenovirus Type 5, Journal General Virology, 1977, pp. 59-72, vol. 36.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Heinis, et al., HIF1a and Pancreatic Beta-Cell Development, The FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

(56) References Cited

OTHER PUBLICATIONS

Heit, et al., Embryonic Stem Cells and Islet Replacement in Diabetes Mellitus, Pediatric Diabetes, 2004, pp. 5-15, vol. 5.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

Herrera, Adult-Insulin-and Glucagon-Producing Cells Differentiate from Two Independent Cell Lineages, Development, 2000, pp. 2317-2322 XP001004766, vol. 127, No. 11.

Herzenberg, et al., Fluorescence-activated Cell Sorting, Scientific American, 1976, 108-117, 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hoffman, et al., Characterization and Culture of Human Embryonic Stem Cells, Nature Biotechnology, 2005, pp. 699-708, vol. 23, No. 6.

Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.

Hosoya, et al., Induction of Differentiation of Undifferentiated Cells into Pancreatic Beta-Cells in Vertebrates, Int. J. Dev. Biol., 2012, pp. 313-323, vol. 56.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, PNAS, May 12, 2009, pp. 7864-7869, vol. 106, No. 19.

Kleinman et al., Basement Membrane Complexes with Biological Activity, Biochemistry, 1986, 312-318, 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Biointerphases, Dec. 2009, pp. 6979.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Konstantinova_et_al_2007, EphA-Ephrin-A-Mediated Beta Cell Communication Regulates Insulin Secretion from Pancreatic Islets, Cell, Apr. 20, 2007, pp. 359-370, vol. 129.

Koyangi et al., Inhibitio nof the Rho/ROCK Pathway Reduces Apoptosis During Transplantatation of Embryonic Stem Cell-Derived Neural Precursors, Journal of Neuroscience Research, Sep. 7, 2007, 270-280, 86, Wiley-Liss, Inc.

Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Lanza, et al., Characteristics and Characterization of Human Pluripotent Stem Cells, Stem Cell Anthology, 2010, pp. 141, 142, 144 and 146, 1st Edition.

(56) References Cited

OTHER PUBLICATIONS

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., Protein Kinase A- and C-Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.

Levenstein et al., Basic Fibroblast Growth Factor Support of Human Embryonic Stem Cell Self-Renewal, Stem Cells, Nov. 10, 2005, 568-574, 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embryonica Stem Cells, Biomaterials, 2009, pp. 1706-1714, vol. 30.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Micallef et al., Retinoic Acid Induces Pdx1-Positive Endoderm in Differentiating Mouse Embryonic Stem Cells, Diabetes, Feb. 2005, 301-305, 54, American Diabetes Association.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Mitalipova, et al., Preserving the Genetic Integrity of Human Embyonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem Cells, Stem Cells, 2004, 433-440, 22, AlphaMed Press.

Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

(56) References Cited

OTHER PUBLICATIONS

Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Pancreatic Endoerm, http://www.rndsystems.com/molecule_group.aspx?g=801&r, 1 page web printout.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Coming CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578 XP009090586, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, http://www.mdsystems.com/molecule_group.aspx?r=1&g-3041, 2 page web printout.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adult Mesenchymal Stem Cells in the CNS, Society for Neuroscience Abstract Viewer and Itinerary Planner, 2002, XP002519394, Program 237.18.

(56) References Cited

OTHER PUBLICATIONS

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Scullica, et al., Diagnosis and Classification of Macular Degenerations: an Approach Based on Retinal Function Testing, Documenta Ophthalmologica, 2001, pp. 237-250, vol. 102.
Seaberg et al., Clonal identification of multipotent precursors from adult ~ mouse pancreas that generate neural and pancreatic lineages, Nature Biotechnology, Sep. 2004, 1115-1124, 22, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points,

(56) References Cited

OTHER PUBLICATIONS

Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Current Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Choice of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vodicka, et al., The Miniature Pig as an Animal Model in Biomedical Research, Annals New York Academy of Sciences, 2005, pp. 161-171, vol. 1049.

Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.

(56) References Cited

OTHER PUBLICATIONS

Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Academy of Military Medical Sciences, 2003, 1-127, 1-127 (with English Abstract).
Zhang et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Ali, et al., Exploitation of Protein Kinase C: A Useful Target for Cancer Therapy, Cancer Treatment Reviews, 2009, pp. 1-8, vol. 35.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Best, et al., Embryonic Stem Cells to Beta-Cells by Understanding Pancreas Development, Molecular and Cellular Endorinology, 2008, pp. 86-94, vol. 288.
Bo, et al., Research Progress of Pancreatic Islet Development and Pancreatic Stem Cells, Journal of Clinical Surgery, 2009, pp. 208-210, vol. 17, No. 3.
Brevini et al, Embryonic Stem Cells in Domestic Animals, Embryonic Stem Cells in Domestic Animals, 2010, 544-550, 74.
Cao, et al., High Glucose is Necssary for Complete Maturation of Pdx1-VP16-Expressing Hepatic Cells into Functional Insulin-Producing Cells, Diabetes, 2004, pp. 3168-3178, vol. 53.
Chen, et al., Retinoic Acid Signaling is Essential for Pancreatic Development and Promotes Endocrine at the Expense of Exocrine Cell Differentiation in Xenopus, Developmental Biology, 2004, pp. 144-160, vol. 271.
Chetty, et al., A Simple Tool to Improve Pluripotent Stem Cell Differentiation, Nature Methods, 2013, pp. 553-558, vol. 10, No. 6.
Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.
D'Amour et al, Production of pancreatic hormone, Production of pancreatic hormone, Nature Biotechnology, 2006, 1392-1401, 24.

Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Florio, et al., Activin A Stimulates Insulin Secretion in Cultured Human Pancreatic Islets, J. Endocrinol. Invest., 2000, pp. 231-234, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gibco, Solutions for Life Science Research and Drug Discovery, Catalogue Cell Culture Products, 2004-2005, pp. 1-4E, 281406 26 5 27.
Gordon Weir, Do stem cells hold the key to creation of a cure for diabetes?, Diabetes Voice, 2008, pp. 29-31, Edition 53, No. 2.
Gregg Duester, Retionoic Acid Synthesis and Signaling During Early Organogenesis, Cell, 2008, pp. 921-931, vol. 134.
Hainsworth, et al., Retinal Capillar Basement Membrane Thickening in a Porcine Model of Diabetes Mellitus, Comp Med, 2002, pp. 523-529, vol. 52.
Harmon, et al., GDF11 Modulates NGN3+ Islet Progenitor Cell Number and Promotes B-Cell Differentiation in Pancreas Development, Development, 2004, pp. 6163-6174, vol. 131.
Hay, et al., Highly Efficient Differentiation of hESCs to Functional Hepatic Endoderm Requires ActivinA and Wnt3a Signaling, PNAS, 2008, pp. 12301-12306, vol. 105, No. 34.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jiang, et al., In Vitro Derivation of Functional Insulin-Producing Cells from Human Embryonic Stem Cells, Cell Research, 2007, pp. 333-344, vol. 17.
Karvonen, et al., Incidene of Childhood Type 1 Diabetes Worldwide, Diabetes Care, 2000, pp. 1516-1526, vol. 23, No. 10.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.
Larsen, et al., Use of the Gootingen Minipig as a Model of Diabetes, with Special Focus on Type 1 Diabetes Research, ILAR Journal, 2004, pp. 303-313, vol. 45, No. 3.
Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Ludwig, et al., Defined Culture Media for Human Embryonic Stem Cells, Embryonic Stem Cells, 2007, pp. 1-16, Springer.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Munoz et al, Conventional pluripotency markers, Theriogenology, 2008, 1159-1164, vol. 69.
Nie, et al., Scalable Passaging of Adherent Human Pluripotent Stem Cells, PLOS One, 2014, pp. 1-9, vol. 9, Issue 1.
Ouziel-Yahalom, et al., Expansion and Redifferentiation of Adult Human Pancreatic islet Cells, Biochemical and Biophysical Research Communications, 2006, pp. 291-298, vol. 341.

(56) References Cited

OTHER PUBLICATIONS

Paris, et al, Embryonic Stem Cells in Domestic Animals, Embryonic Stem Cells in Domestic Animals, 2010, 516-524, 74.
Park, et al., Effects of Activin A on Pancreatic Ductal Cells in Streptozotocin-Inducted Diabetic Rats, Experimental Transplantation, 2007, pp. 925-930, vol. 83.
Perrier, et al., Derivation of Midbrain Dopamine Neurons from Human Embryonic Stem Cells, PNAS, Aug. 24, 2004, pp. 12543-12548, vol. 101, No. 34.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-282, vol. 6.
Rezania, E Al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania, et al., Enrichman of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Richards, et al., Development of Defined Media for the Serum-Free Expansion of Primary Keratinocytes and Human Embryonic Stem Cells, Tissue Engineering, 2008, pp. 221-232, vol. 14, No. 3.
Ross, et al., Cytochrome P450s in the Regulation of Cellular Retinoic Acid Metabolism, Annu. Rev. Nutr., 2011, pp. 65-87, vol. 31.
Rowley, et al., Meeting Lot-Size Challenges of Manufacturing Adherent Cells for Therapy, Cell Therapies Manufacturing, 2012, pp. 16-22, vol. 10, No. 3.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schulz, et al., A Scalable System for Production of Functional Pancreatic Progenitors from Human Embryonic Stem Cells, PLOS One, 2012, pp. 1-17, vol. 7, Issue 5.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Soria, et al., From Stem Cells to Beta Cells: New Strategies in Cell Therapy of Diabetes Mellitus, Diabetologia, 2001, pp. 407-415, vol. 44.
Stacpoole, et al., Efficient Derivation of Neural Precuros Cells, Spinal Motor Neurons and Midbr, Nat Protoc, 2012, pp. 1-26, vol. 6, Issue 8.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Tsuchida, et al., Activin Isoforms Signal Through Type I Receptor Serine/Threonin Kinase ALK7, Molecular and Cellular Endocrinology, 2004, pp. 59-65, vol. 22.
Vieira, et al., Modulation of Neuronal Stem Cell Differentiation by Hypoxia and Reactive Oxygen Species, Progress in Neurobiology, 2011, pp. 444-455, vol. 93.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang, et al., Evaluation of Humam MSCs Cell Cycle, Viability and Differentiation in Micromass Culture, Biorheology, 2006, p. 489-496, vol. 43 (Abstract Only).
Zalzman, et al., Differentiation of Human Liver-Derived, Insulin-Producing Cells Toward the B-Cell Phenotype, Diabetes, 2005, pp. 2568-2575, vol. 54.
Zuscik, et al., Regulation of Chondrogenesis and Chondrocyte Differentiation by Stress, J Clin Invest, 2008, pp. 429-438, vol. 118, Issue 2.
Tsanarias, S. and Jones, P., Generating pancreatic β-cells from embryonic stem cells by manipulating signaling pathways, Journal of Endocrinology, 2010, pp. 13-26, vol. 206.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Brimble, S., et al., The Cell Surface Glycosphingolipis SSEA-3 and SSEA-4 Are Not Essential for Human ESC Pluripotency, Stem Cells, Jan. 2007, pp. 54-62, vol. 25.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Chen, et al., Scalable GMP Compliant Suspension Culture System for Human ES Cells, Stem Cell Research, 2012, pp. 388-402, vol. 8.
Cirulli, et al., Netrins: beyond the brain, Molecular Cell Biology, Apr. 2007, pp. 296-306, vol. 8.
Furue, et al., Heparin propotes the growth of human embryonic stem cells in a defined serum-free medium, PNAS, Sep. 9, 2008, pp. 13409-13414, vol. 105, Issue 36.
Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir, Do stem cells hold the key to a future cure for diabetes?, DiabetesVoice, Jun. 2008, pp. 29-31, vol. 53, Issue 2.
Guo, et al., Efficient differentiation of insulin-producing cells from skin-derived stem cells, Cell Proliferation, 2009, pp. 49-62, vol. 42.
Hiemisch, H., et al., Transcriptional Regulation in Endoderm Development: Characterization of an Enhancer Controlling Hnf3g Expression by Transgenesis and Targeted Mutagenesis, The EMBO Journal, 1997, 3995-4006, vol. 16(13).
Jean, et al., Pluripotent genes in avian stem cells, Development Growth & Differentitaion, 2013, pp. 41-51, vol. 55.
Kang, et al., Plasma treatment of textiles—Synthetic Polymer-Based Textiles, AATCC Review, 2004, pp. 29-33, vol. 4.
King, et al., Bioreactor development for stem cell expansion and controlled differentiation, Current Opinion in Chemical Biology, Jul. 25, 2007, pp. 394-398, vol. 11, Elsevier Ltd.
Kunisada, et al., Small molecules induce efficient differentiation into insulin-producing cells from human induced pluripotent stem cells, Stem Cell Research, Oct. 11, 2011, pp. 274-284, vol. 8.
Lavial, et al., Chicken Embryonic Stem Cells as a Non-Mammalian Ebryonic Stem Cell Model, Development Growth Differentiation, Jan. 2010, pp. 101-114, vol. 52(1).
Lin, C., et al., Coagulation Dysregulatin as a Barrier to Xenotransplantation n the Primate, Transplant Immunology, 2009, pp. 75-80, vol. 21.

(56) References Cited

OTHER PUBLICATIONS

Maria-Jesus Obregon, Thyroid hormone and adipocyte differentiation, Thyroid, 2008, pp. 185-195, vol. 18, Issue 2.
McMahon, et al., Noggin-mediated antagonsim of BMP signaling is required for growth and patterning of the neural tube and somite, Genes & Development, Mar. 16, 1998, pp. 1438-1452, vol. 12.
Nakase, et al., Myeliod Antigen, CD13, CD14, and/ or CD33 Expression Is Restricted to Certain Lymphiod Neoplasms, Hematopathology, Jun. 1996, pp. 761-768, vol. 105, Issue 6.
Narang, A., et al., Biological and Biomaterial Approaches for Improved Islet Transplantation, Pharmacological Review, Jun. 2006, pp. 194-243, vol. 58(2).
Olmer, et al., Long Term Expansion of Undifferentiated Human iPS and ES Cells in Suspension Culture Using Defined Medium, Stem Cell Research, 2010, pp. 51-64, vol. 5.
Ouziel-Yahalom, et al., Expansion and redifferentiation of adult human pancreatic islet cells, Biochemical and Biophysical Research Communications, Jan. 19, 2006, pp. 291-298, vol. 341.
Petitte, J., et al., Avian Plluripotent Stem Cells, Mechanisms of Development, 2004, pp. 1159-1168, vol. 121.
Ramiya, et al., Reversal of insulin-dependent diabetes using islets generated in vitro from pancreatic stem cells, Nature Medicine, Mar. 2000, pp. 278-282, vol. 6, Issue 3.
Rother, et al., Challenges facing islet transplantation for the treatment of type 1 diabetes mellitus, The Journal Of Clinical Investigation, 2004, pp. 877-883, vol. 114, Issue 7.
Rowely, et al., Meeting Lot-size Challenges of Manufacturing Adherent Cells for Therapy, Bio Process International, Mar. 2012, pp. 16-22, vol. 10 Issue 3.
Sjögren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
Thomson, Bioprocessing of Embryonic Stem Cells for Drug Disvoery, Trends in Biotechnology, 2007, pp. 224-230, vol. 25, No. 5.
Yadlin, et al., Small-molecule inducers of insulin expression in pancreatic α-cells, PNAS, Aug. 24, 2010, pp. 15099-15104, vol. 107, Issue 34.
Yang JW, et al., Evaluation of human MSCs cell cycle, viability and differentiation in micromass culture, Biorheology, 2006, pp. 1-2, vol. 43, Issue (3-4).
Yim,et al., Proliferation and differentiation of human embryonic germ cell derivatives in bioactive polymeric fibrous scaffold, J.Biomater. Sci.Polymer Edn,, Jan. 19, 2005, pp. 1193-1217, vol. 16 Issue 10.
Zulewski, et al., Multipotentital Nestin-Positive Stem Cells Iasolated From Adult Pancreatic Islets Differentiate Ex Vivo Into Pancreatic Endocrine, Exocrine, and Hepatic Phenotypes, Diabetes, 2001, pp. 521-533, vol. 50.
Cohick, et al., The Insulin-Like Growth Factors, Annual Reviews Physiol, 1993, pp. 131-153, vol. 55, Annual Reviews Inc.
Hebrok, et al., Notochord repression of endodermal Sonic hedgehog permits pancreas development, Genes & Development, Jun. 1, 1998, pp. 1705-1713, vol. 12 , Issue 11, Cold Spring Harbor Laboratory Press.
Jaenisch, et al., Stem Cells, the Molecular Circuitry of Pluripotency and Nuclear Reprogramming, cell, Feb. 22, 2008, pp. 567-582, vol. 132, Elsevier Inc.
Klajnert, et al., Fluorescence studies on PAMAM dendrimers interactions with bovine serum albumin, Bioelectrochemistry, 2002, pp. 33-35, vol. 55.
Kubota,et al., Growth factors essential for self-renewal and expansion of mouse spermatogonial stem cells, cell Biology, Nov. 23, 2004, pp. 16489-16494, vol. 101 , Issue 47.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34 , Issue 4.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182 , Issue 2.
Balajthy, et al., Molecular therapies., Molecular therapies, 2011, pp. 1-6.
Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.
Daheron, et al., LIF/STAT3 Signaling Fails to Maintain Self-Renewal of Human Embryonic Stem Cells, Stem Cells, 2004, pp. 770-778, vol. 22.
Findikli, et al., Establishment and characterization of new human embryonic stem cell lines, Reproductive BioMedicine Online, Mar. 3, 2005, pp. 617-627, vol. 10 Issue 5.
Foster, et al., Differentiation of Transplanted Microencapsulated Fetal Pancreatic Cells, Transplantation, Jun. 15, 2007, pp. 1440-1448, vol. 83 Issue 11.
Guillemain, et al., Glucose Is Necessary For Embryonic Pancreatic Endocrine Cell Differentiation*, The Journal Of Biological Chemistry, May 18, 2007, pp. 15228-15237, vol. 282 Issue 20.
Kehoe, et al., Scalable Stirred-Suspension Bioreactor Culture of Human Pluripotent Stem Cells, Tissue Eng Part A, 2010, pp. 405-421, vol. 16 Issue 2.
Kim, et al., Reprogrammed Pluripotent Stem Cells from Somatic Cells, International Journal of Stem Cells, 2011, pp. 1-8, vol. 4 Issue 1.
Lee, et al., Available human feeder cells for the maintenance of human embryonic stem cells, Reproduction, 2004, pp. 727-735, vol. 128.
Ludwig, et al., Defined, Feeder-Independent Medium For human Embryonic Stem Cell Culture, Current Protocols In Stem Cell Biology, 2007, pp. 1C.2.1-1C.2.16, vol. 1, John Wiley & Sons, Inc.
Maimets, et al., Activation of p53 by nutlin leads to rapid differentiation of human embryonic stem cells, Oncogene, Jun. 2, 2008, pp. 5277-5287, vol. 27.
Micallef, et al., Pancreas Differentiation of Mouse ES Cells, Current Protocols in Stem Cell Biology, 2007, pp. 1G.1.1-1.2.8.
Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.
Nakanishi, et al., Pancreatic tissue formation from murine embryonic stem cells in vitro, Differentiation, 2007, pp. 1-11, vol. 75.
Nekrasov, et al., Induced pluripotent stem cells as a model for studying human diseases, Cellular Transplantology and Tissue Engineering, 2011, pp. 32-37, vol. 6 Issue 2.
Osafune, et al., Marked differences in differentiation propensity among human embryonic stem cell lines, Nature Biotechnology, Feb. 17, 2008, pp. 313-315, vol. 26 Issue 3.
Sigma-Aldrich, MCDB-131 product description, Sigma-Aldrich, 2007, pp. 1-2, page number.
Verkhovskaya, et al., Effect of alkoxy-substituted of glycerin on the morphofunctional properties of continuous cell culture, Cryobiology, 1990, pp. 30-33, vol. 1.
Wang, et al., Cultivation and identification of pancreatic endocrine progenitor cells, National Medical Journal of China, 2006, pp. 1850-1853, vol. 86 Issue 26.
Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.
Zhu, et al., A Small Molecule Primes Embryonic Stem Cells for Differentiation, Cell Stem Cell, May 8, 2009, pp. 416-426, vol. 4.
Sui, et al. Stem Cell Therapy for Diabetes: A Call for Efficient Differentiation of Pancreatic Progenitors, J. Regenerative Medicine 2013, vol. 2, No. 1.

(56) References Cited

OTHER PUBLICATIONS

Zorn, et al., Vertebrate Endoderm Development and Organ Formation, Annual Review Cell Development Biology, Aug. 12, 2009, pp. 221-251, vol. 25.
Jennings, R.E. et al., Development of the Human Pancreas from Foregut to Endocrine Commitment, Diabetes, 2013, pp. 3514-3622, vol. 62, No. 10.
Murtaugh, et al., Notch Signaling Controls Multiple Steps of Pancreatic Differentiation, 2003, PNAS, vol. 100, No. 25, pp. 14920-14925.
Nishimura et al., A Switch from MafB to MafA Expression Accompanies Differentiation to B-Cells, Developmental Biology, 2006, vol. 293, pp. 526-539.
Pagliuca, F.W., et al., How to Make a Functional Beta-Cell, Development, Jun. 15, 2013, pp. 2472-2483, vol. 140, No. 12.

* cited by examiner

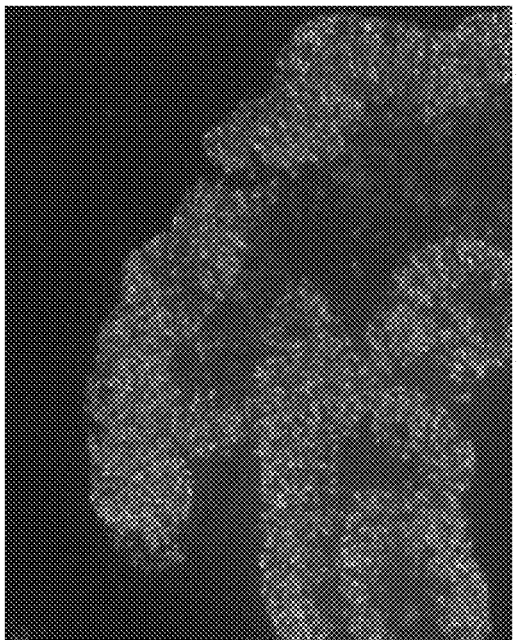
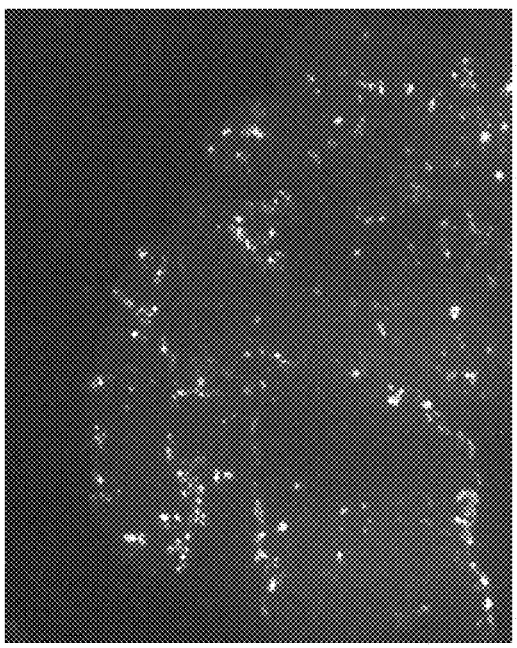
FIG. 3A
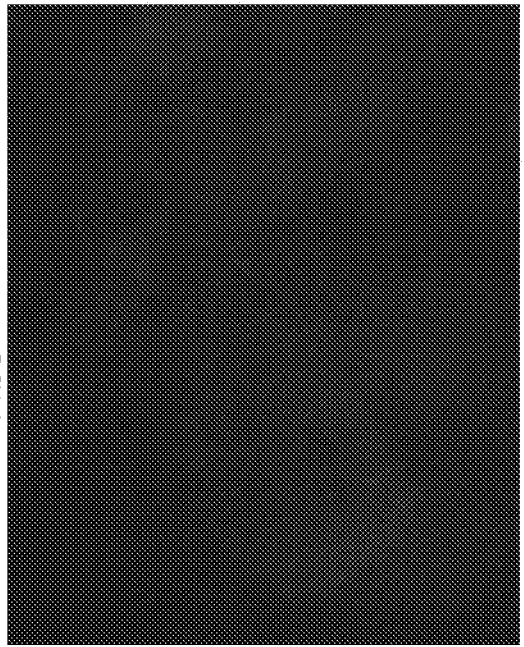
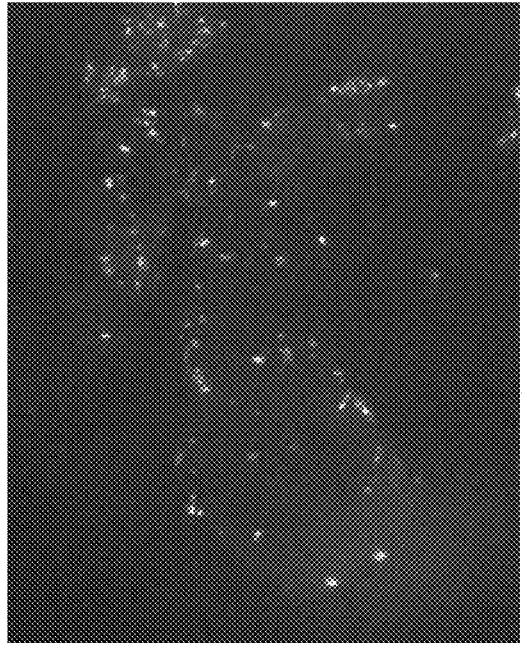
FIG. 3B

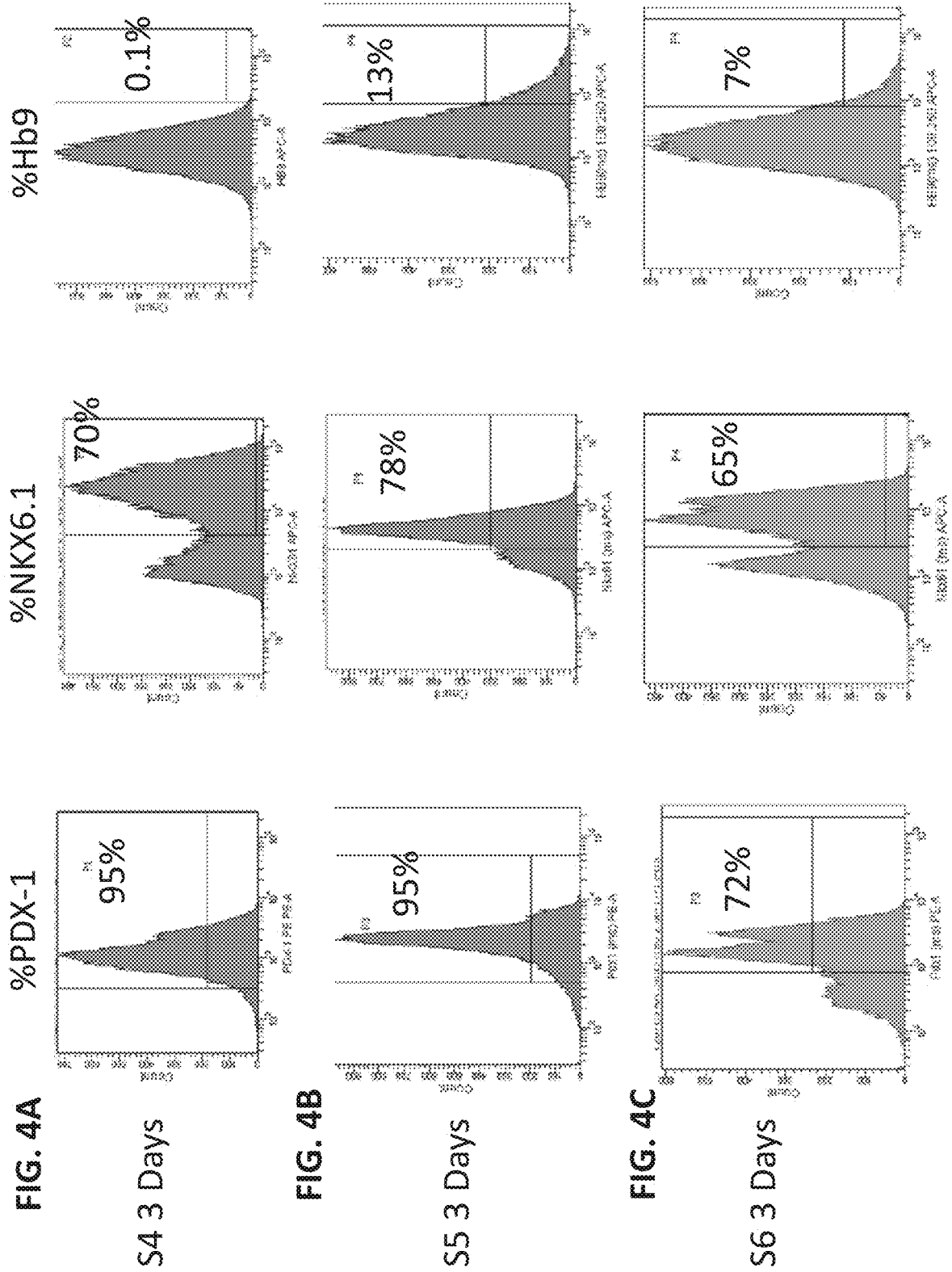

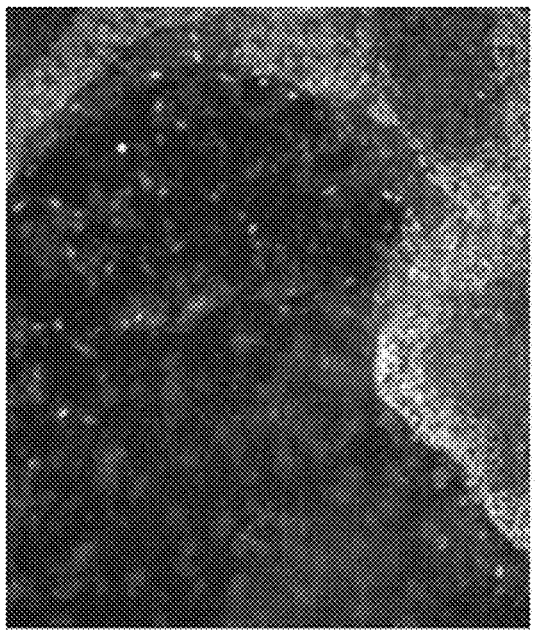
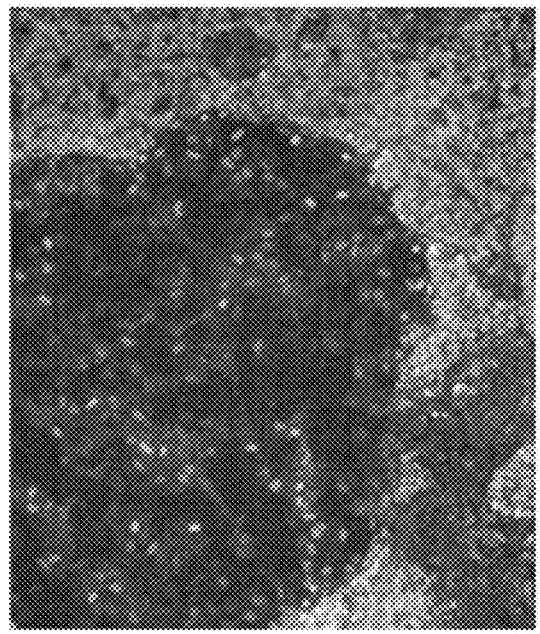
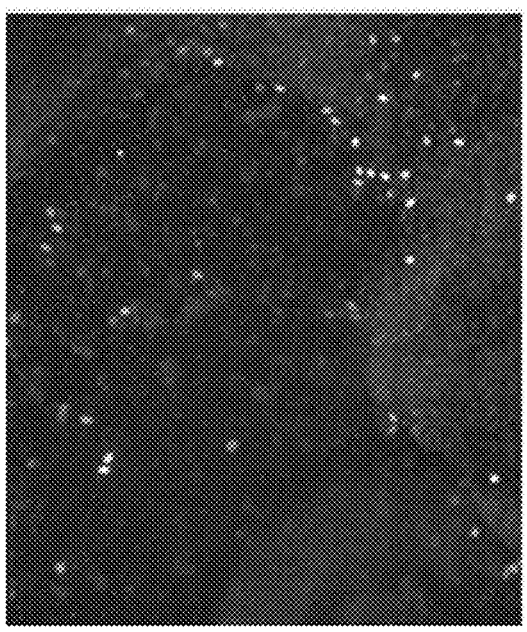
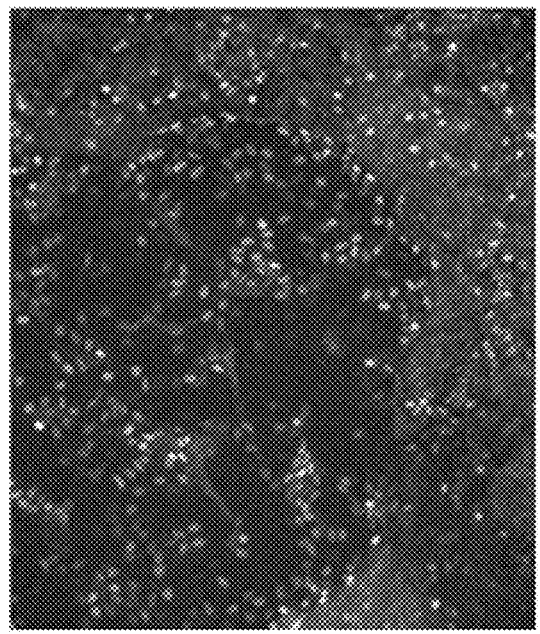
FIG. 7A
FIG. 7B

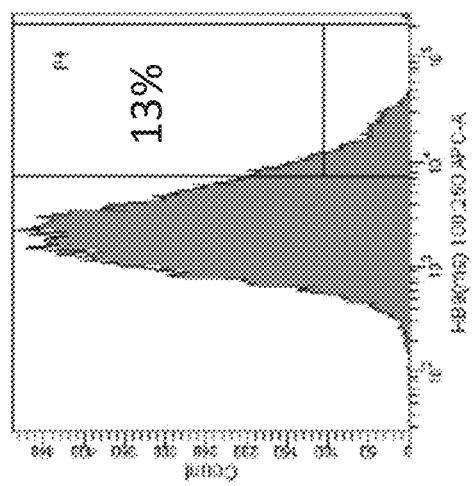
FIG. 9A
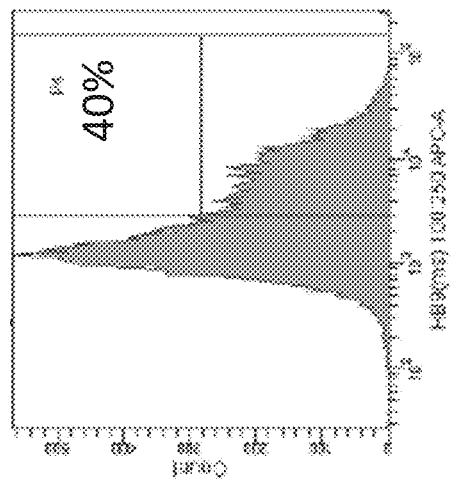
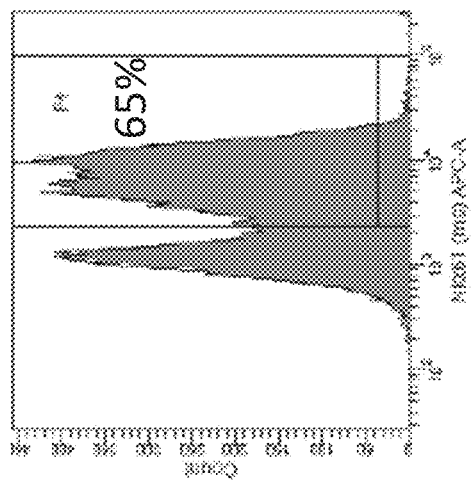
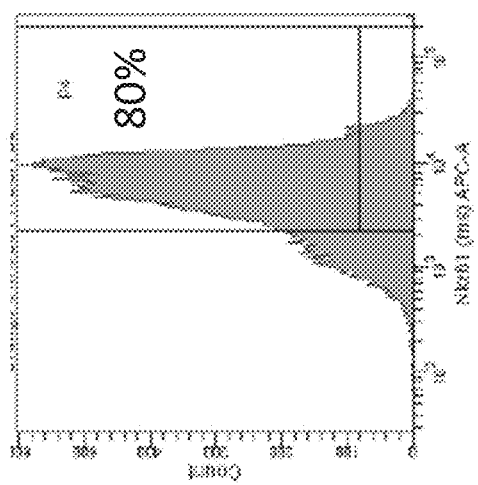
FIG. 9B

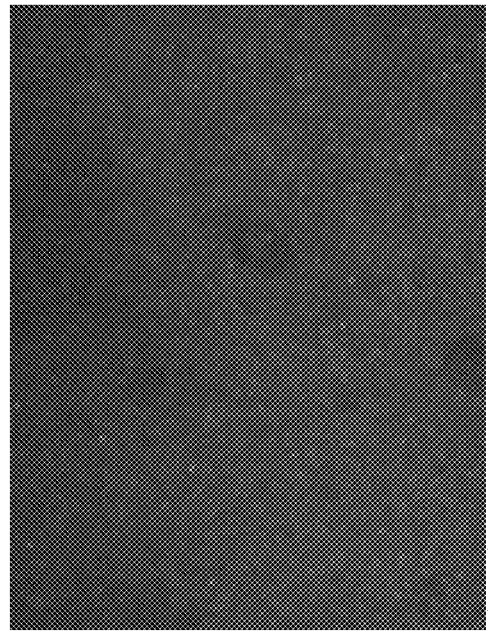
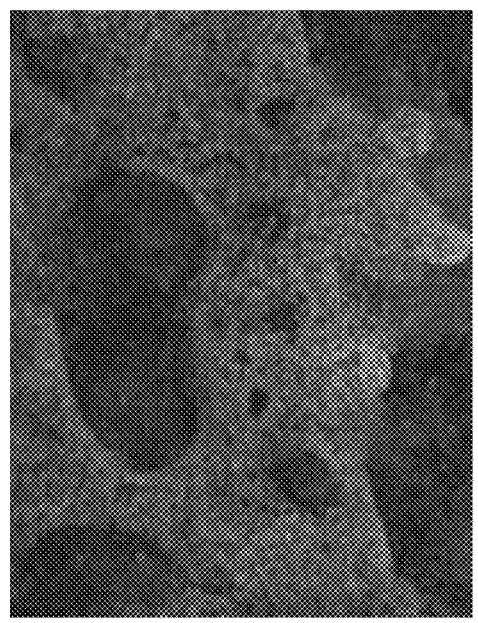
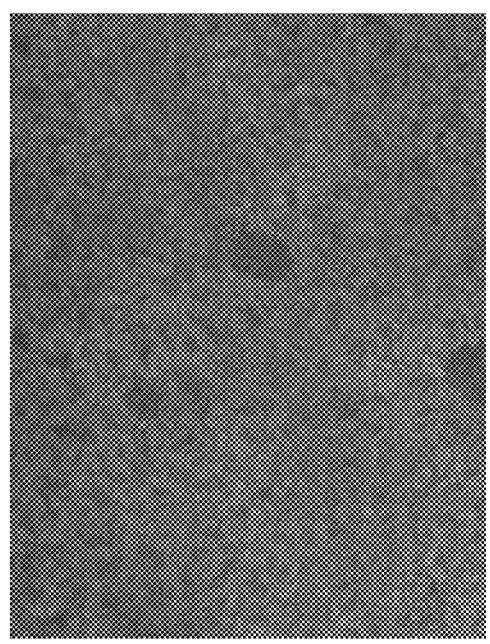
FIG. 10A
FIG. 10B

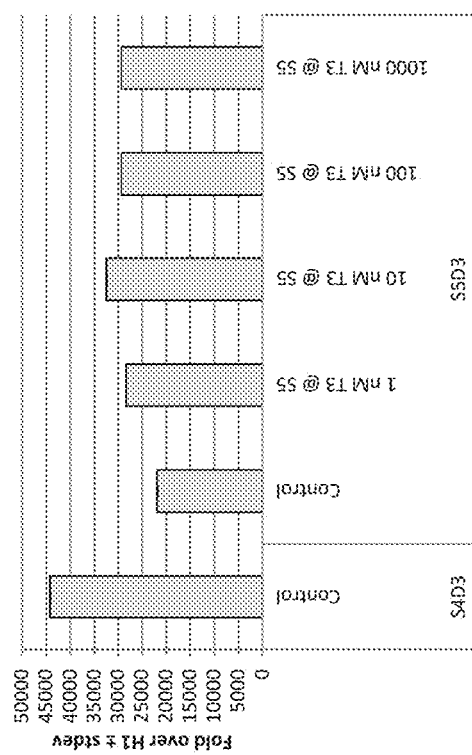
FIG. 11A
FIG. 11B
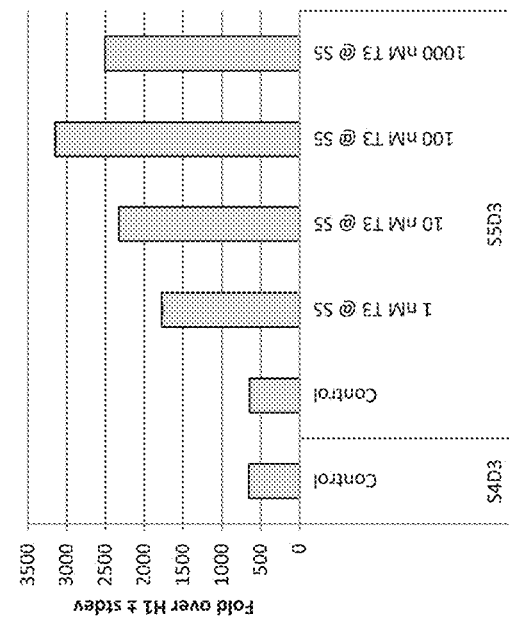
FIG. 11C
FIG. 11D

DIFFERENTIATION OF HUMAN EMBRYONIC STEM CELLS INTO PANCREATIC ENDOCRINE CELLS USING THYROID HORMONE AND/OR ALK5, AN INHIBITOR OF TGF-BETA TYPE 1 RECEPTOR

CROSS-REFERENCE TO RELATED APPLICATIONS

This application a divisional application of U.S. application Ser. No. 13/998,883 (filed on Dec. 18, 2013 (now allowed)), which claims priority to U.S. Provisional Application 61/747,672 (filed on Dec. 31, 2012) the entire contents of which are incorporated by reference in their entireties.

FIELD OF THE INVENTION

The present invention is in the field of cell differentiation. More specifically, the invention involves the use of specific thyroid hormones, or analogues thereof, and ALK5 inhibitors as regulators of HB9 in pancreatic endoderm and endocrine cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. The intermediate stage in this process is the formation of definitive endoderm.

By the end of gastrulation, the endoderm is partitioned into anterior-posterior domains that can be recognized by the expression of a panel of factors that uniquely mark anterior, mid, and posterior regions of the endoderm. For example, HHEX, and SOX2 identify the anterior region while CDX1, 2, and 4 identify the posterior region of the endoderm.

Migration of endoderm tissue brings the endoderm into close proximity with different mesodermal tissues that help in regionalization of the gut tube. This is accomplished by a plethora of secreted factors, such as FGFs, WNTs, TGF-βs, retinoic acid (RA), and BMP ligands and their antagonists. For example, FGF4 and BMP promote CDX2 expression in the presumptive hindgut endoderm and repress expression of the anterior genes HHEX and SOX2 (2000 *Development*, 127:1563-1567). WNT signaling has also been shown to work in parallel to FGF signaling to promote hindgut development and inhibit foregut fate (2007 *Development*, 134:2207-2217). Lastly, secreted retinoic acid by mesenchyme regulates the foregut-hindgut boundary (2002 *Curr Biol*, 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. The regionalized pancreas domain in the gut tube shows a very high expression of PDX1 and very low expression of CDX2 and SOX2. PDX1, NKX6.1, PTF1A, and NKX2.2 are highly expressed in pancreatic tissue; and expression of CDX2 is high in intestinal tissue.

Formation of the pancreas arises from the differentiation of definitive endoderm into pancreatic endoderm. Dorsal and ventral pancreatic domains arise from the foregut epithelium. Foregut also gives rise to the esophagus, trachea, lungs, thyroid, stomach, liver, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains both exocrine and endocrine tissues arising from the differentiation of pancreatic endoderm.

D'Amour et al. describe the production of enriched cultures of human embryonic stem cell-derived definitive endoderm in the presence of a high concentration of activin and low serum (*Nature Biotechnology* 2005, 23:1534-1541; U.S. Pat. No. 7,704,738). Transplanting these cells under the kidney capsule of mice reportedly resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF10 and retinoic acid (U.S. Patent App. Pub. No. 2005/0266554). Subsequent transplantation of these pancreatic precursor cells in the fat pad of immune deficient mice resulted in the formation of functional pancreatic endocrine cells following a 3-4 months maturation phase (U.S. Pat. Nos. 7,993,920 and 7,534,608).

Fisk et al. report a system for producing pancreatic islet cells from human embryonic stem cells (U.S. Pat. No. 7,033,831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-β receptor and BMP receptors (*Development* 2011, 138:861-871; *Diabetes* 2011, 60:239-247) have been used to significantly enhance the number of pancreatic endocrine cells. In addition, small molecule activators have also been used to generate definitive endoderm cells or pancreatic precursor cells (*Curr Opin Cell Biol* 2009, 21:727-732; *Nature Chem Biol* 2009, 5:258-265).

HB9 (also known as H1XB9 and MNX1) is a bHLH transcriptional activator protein expressed early in pancreas development starting at approximately embryonic day 8. HB9 is also expressed in notochord and spinal cord. Expression of HB9 is transient and peaks at about day 10.5 in pancreatic epithelium being expressed in PDX1 and NKX6.1 expressing cells. At about day 12.5, HB9 expression declines and at later stages it becomes restricted only to β cells. In mice homozygous for a null mutation of H1XB9, the dorsal lobe of the pancreas fails to develop (*Nat Genet* 23:67-70, 1999; *Nat Genet* 23:71-75, 1999). HB9−/− β-cells express low levels of the glucose transporter, GLUT2, and NKX6.1. Furthermore, HB9−/− pancreas shows a significant reduction in the number of insulin positive cells while not significantly affecting expression of other pancreatic hormones. Thus, temporal control of HB9 is essential to normal β cell development and function. While not much is known about factors regulating HB9 expression in β cells, a recent study in zebrafish suggests that retinoic acid can positively regulate expression of HB9 (*Development*, 138, 4597-4608, 2011).

The thyroid hormones, thyroxine ("T4") and triiodothyronine ("T3"), are tyrosine-based hormones produced by the thyroid gland and are primarily responsible for regulation of metabolism. The major form of thyroid hormone in the blood is T4, which has a longer half-life than T3. The ratio of T4 to T3 released into the blood is roughly 20 to 1. T4 is converted to the more active T3 (three to four times more potent than T4) within cells by deiodinase.

T3 binds to thyroid hormone receptors, TRα1 and TRβ1 (TR). TR is a nuclear hormone receptor, which heterodimerizes with retinoid X receptor. The dimers bind to the thyroid response elements (TREs) in the absence of ligand and act as transcriptional repressors. Binding of T3 to TR reduces the repression of TRE dependent genes and induces the expression of various target genes. While numerous studies have suggested a role for T3 in increasing β cell proliferation, reducing apoptosis, and improving insulin secretion, its role in cell differentiation is undefined.

Transforming growth factor β (TGF-β) is a member of a large family of pleiotropic cytokines that are involved in many biological processes, including growth control, differentiation, migration, cell survival, fibrosis and specification of developmental fate. TGF-β superfamily members signal through a receptor complex comprising a type II and type I receptor. TGF-B ligands (such as activins, and GDFs (growth differentiation factors)) bring together a type II receptor with a type I receptor. The type II receptor phosphorylates and activates the type I receptor in the complex. There are five mammalian type II receptors: TβR-II, ActR-II, ActR-IIB, BMPR-II, and AMHR-II and seven type I receptors (ALKs 1-7). Activin and related ligands signal via combinations of ActR-II or ActR-IIB and ALK4 or ALK5, and BMPs signal through combinations of ALK2, ALK3, and ALK6 with ActR-II, ActR-IIB, or BMPR-II. AMH signals through a complex of AMHR-II with ALK6, and nodal has been shown recently to signal through a complex of ActR-IIB and ALK7 (*Cell*. 2003, 113(6):685-700). Following binding of the TGF-B ligand to the appropriate receptor, the ensuing signals are transduced to the nucleus primarily through activation of complexes of Smads. Upon activation, the type I receptors phosphorylate members of the receptor-regulated subfamily of Smads. This activates them and enables them to form complexes with a common mediator Smad, Smad4. Smads 1, 5, and 8 are substrates for ALKs 1, 2, 3, and 6, whereas Smads 2 and 3 are substrates for ALKs 4, 5, and 7 (*FASEB J* 13:2105-2124). The activated Smad complexes accumulate in the nucleus, where they are directly involved in the transcription of target genes, usually in association with other specific DNA-binding transcription factors. Compounds that selectively inhibit the receptors for TGF-β, have been developed for therapeutic applications and for modulating cell fate in the context of reprogramming and differentiation from various stem cell populations. In particular, ALK5 inhibitors have been previously used to direct differentiation of embryonic stem cells to an endocrine fate (*Diabetes*, 2011, 60(1):239-47).

In general, the process of differentiating progenitor cells to functional β cells goes through various stages. Yet it is recognized that directing human embryonic stem ("hES") cells in vitro progressively through stages of commitment to cells resembling β-cells is challenging and production of functional β-cells from hES cells is not a straightforward process. Each step in the process of differentiating progenitor cells presents a unique challenge. Although progress has been made in improving protocols to generate pancreatic cells from progenitor cells such as human pluripotent stem cells, there is still a need to generate a protocol that results in functional endocrine cells and, in particular, β cells.

BRIEF DESCRIPTION OF THE DRAWINGS

FIGS. 3A and 3B show images of cells immunostained for NXK6.1, insulin or HB9. The cells were differentiated to pancreatic endoderm/endocrine precursors as outlined in Example 1. FIG. 3A shows immune staining for NKX6.1 (left hand pane) and insulin (right hand pane). FIG. 3B shows immune staining for HB9 (left hand pane) and insulin (right hand pane).

FIGS. 4A, 4B, and 4C depict the FACS data for percent expression of PDX1, NKX6.1, and HB9 at Stage 4 day 3 (FIG. 4A), Stage 5 day 4 (FIG. 4B) and Stage 6 day 3 (FIG. 4C) of embryonic stem cell line H1 differentiated to Stages 4 through 6 as outlined in Example 2.

FIG. 5A shows mRNA expression of HB9 as compared to human islets at Stages 2 through 6 for cells differentiated as outlined in Example 2.

FIG. 5B depicts images of Stage 4 day 3 cells, which were differentiated as outlined in Example 2, immunostained for NXK6.1 (left hand pane) and HB9 (right hand pane).

FIGS. 6A to 6J depict the data for the following: NKX6.1 (FIG. 6A); PDX1 (FIG. 6B); NKX2.2 (FIG. 6C); glucagon (FIG. 6D); insulin (FIG. 6E); somatostatin (FIG. 6F); CDX2 (FIG. 6G); albumin (FIG. 6H); gastrin (FIG. 6I); and SOX2 (FIG. 6J).

FIGS. 7A and 7B show the results of immunostaining of control (FIG. 7A) and cultures treated (FIG. 7B) as outlined in Example 2. Immunostaining of control (FIG. 7A) and treated cultures (FIG. 7B) at Stage 6 revealed a significant increase in the number of HB9 positive cells in the T3 treated group (FIG. 7B) as compared to the control (FIG. 7A) at Stage 6.

FIG. 8C depicts data from real-time PCR analyses of the expression of the HB9 in cells of the human embryonic stem cell line H1 differentiated to Stage 6 as outlined in Example 3.

FIGS. 9A and 9B depict the FACS data at Stage 6 day 5 and day 15, respectively, of the HB9 in cells of the human embryonic stem cell line H1 differentiated to Stage 6 as outlined in Example 3.

FIGS. 10A to 10E depict immunostaining for NKX6.1 and HB9 at Stage 6 day 6 for cells that were differentiated according to the protocol outlined in Example 4. T3 in a dose dependent manner significantly enhanced the number of HB9 positive cells in the NKX6.1 positive pancreatic endoderm precursor cells.

FIGS. 11A to 11L depict data from real-time PCR analyses of the expression of the following genes in cells of the human embryonic stem cell line H1 differentiated to Stage 6 as outlined in Example 4: SOX2 (FIG. 11A); NKX6.1 (FIG. 11B); NKX2.2 (FIG. 11C); gastrin (FIG. 11D); PDX1 (FIG. 11E); NGN3 (FIG. 11F); PAX6 (FIG. 11G); PAX4 (FIG. 11H); insulin (FIG. 11I); glucagon (FIG. 11J); ghrelin (FIG. 11K); and somatostatin (FIG. 11L).

DETAILED DESCRIPTION

Figure 1A:
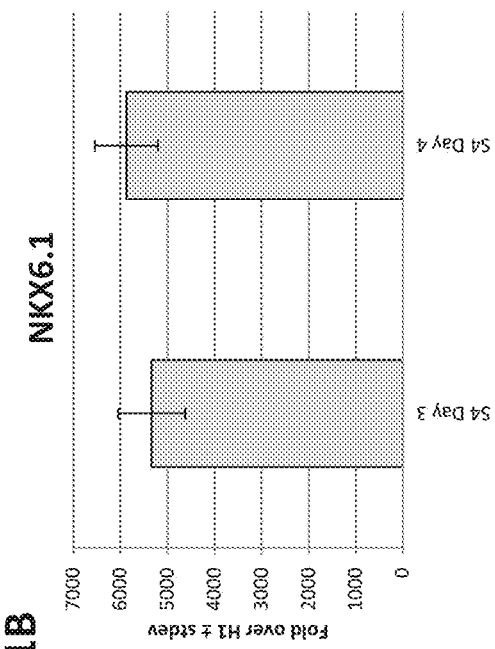
FIGS. 1A to 1C depict data from real-time PCR analyses of the expression of the following genes in cells of the human embryonic stem cell line H1 differentiated to pancreatic endoderm/endocrine precursors as outlined in Example 1: PDX1 (FIG. 1A); NKX6.1 (FIG. 1B); and HB9 (FIG. 1C).

The following detailed description of the invention, will be better understood when read in conjunction with the appended figures. Figures are provided for the purpose of illustrating certain embodiments of the invention. However, the invention is not limited to the precise arrangements, examples, and instrumentalities shown. For clarity of disclosure, and not by way of limitation, the detailed description of the invention is divided into subsections that describe or illustrate certain features, embodiments, or applications of the present invention.

The present invention pertains to the generation of pancreatic endoderm cells that are positive for NKX6.1, PDX1, and HB9 via use of certain thyroid hormones, or analogues thereof, and ALK5 (TGFβ type I receptor kinase) inhibitors in a specific culturing sequence. Accordingly, the present invention provides an in vitro cell culture for differentiating cells derived from pluripotent stem cells into cells expressing markers characteristic of the β cell lineage that express NKX6.1, PDX1 and HB9. The invention further provides a method for obtaining such cells via an in vitro cell culture. In certain embodiments, the invention is based on the discovery that the inclusion of T3, T4, or analogues thereof, act as an inducer of HB9 protein expression in differentiating cells to facilitate differentiation towards β cells. HB9 is not expressed at the protein level at Stage 3 or Stage 4. Accordingly, the present invention provides methods of differentiating stem cells by regulating HB9 protein expression. In particular, this invention provides for the generation of pancreatic endoderm cells that are positive for NKX6.1, PDX1, and HB9 via use of T3 or T4, or analogues thereof, and ALK5 inhibition in a specific culturing sequence.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm, and ectoderm). Stem cells also give rise to tissues of multiple germ layers following transplantation and contribute substantially to most, if not all, tissues following injection into blastocysts.

Stem cells are classified by their developmental potential. Pluripotent stem cells are able to give rise to all embryonic cell types.

Differentiation is the process by which an unspecialized ("uncommitted") or less specialized cell acquires the features of a specialized cell such as, for example, a nerve cell or a muscle cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is sufficiently detected in the cell. Similarly, the cell is "negative for" a specific marker, or "negative" when the specific marker is not sufficiently detected in the cell. In particular, positive by FACS is usually greater than 2%, whereas the negative threshold by FACS is usually less than 1%. Positive by PCR is usually less than 34 cycles (Cts); whereas negative by PCR is usually more than 34.5 cycles.

In attempts to replicate the differentiation of pluripotent stem cells into functional pancreatic endocrine cells in static in vitro cell cultures, the differentiation process is often viewed as progressing through a number of consecutive stages. In particular, the differentiation process is commonly viewed as progressing through six stages. In this step-wise progression, "Stage 1" refers to the first step in the differentiation process, the differentiation of pluripotent stem cells into cells expressing markers characteristic of definitive endoderm cells (hereinafter referred to alternatively as "Stage 1 cells"). "Stage 2" refers to the second step, the differentiation of cells expressing markers characteristic of definitive endoderm cells into cells expressing markers characteristic of gut tube cells (hereinafter referred to alternatively as "Stage 2 cells"). "Stage 3" refers to the third step, the differentiation of cells expressing markers characteristic of gut tube cells into cells expressing markers characteristic of foregut endoderm cells (hereinafter referred to alternatively as "Stage 3 cells"). "Stage 4" refers to the fourth step, the differentiation of cells expressing markers characteristic of foregut endoderm cells into cells expressing markers characteristic of pancreatic foregut precursor cells (hereinafter referred to alternatively as "Stage 4 cells"). "Stage 5" refers to the fifth step, the differentiation of cells expressing markers characteristic of pancreatic foregut precursor cells into cells expressing markers characteristic of pancreatic endoderm cells and/or pancreatic endocrine precursor cells (hereinafter referred to collectively as "pancreatic endoderm/endocrine precursor cells" or alternatively as "Stage 5 cells"). "Stage 6" refers to the differentiation of cells expressing markers characteristic of pancreatic endoderm/ endocrine precursor cells into cells expressing markers characteristic of pancreatic endocrine cells (hereinafter referred to alternatively as "Stage 6 cells").

However, it should be noted that not all cells in a particular population progress through these stages at the same rate. Consequently, it is not uncommon in in vitro cell cultures to detect the presence of cells that have progressed less, or more, down the differentiation pathway than the majority of cells present in the population, particularly at the later differentiation stages. For example, it is not uncommon to see the appearance of markers characteristic of pancreatic endocrine cells during the culture of cells at Stage 5. For purposes of illustrating the present invention, characteristics of the various cell types associated with the above-identified stages are described herein.

"Definitive endoderm cells," as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3-β ("HNF3β")), GATA4, SOX17, CXCR4, Brachyury, Cerberus, OTX2, goosecoid, C-Kit, CD99, and MIXL1. Markers characteristic of the definitive endoderm cells include CXCR4, FOXA2 and SOX17. Thus, definitive endoderm cells may be characterized by their expression of CXCR4, FOXA2 and SOX17. In addition, depending on the length of time cells are allowed to remain in Stage 1, an increase in HNF4a may be observed.

"Gut tube cells," as used herein, refers to cells derived from definitive endoderm that can give rise to all endodermal organs, such as lungs, liver, pancreas, stomach, and intestine. Gut tube cells may be characterized by their substantially increased expression of HNF4α over that expressed by definitive endoderm cells. For example, a ten to forty fold increase in mRNA expression of HNF4α may be observed during Stage 2.

"Foregut endoderm cells," as used herein, refers to endoderm cells that give rise to the esophagus, lungs, stomach, liver, pancreas, gall bladder, and a portion of the duodenum. Foregut endoderm cells express at least one of the following markers: PDX1, FOXA2, CDX2, SOX2, and HNF4α. Foregut endoderm cells may be characterized by an increase in expression of PDX1 compared to gut tube cells. For example, greater than fifty percent of the cells in Stage 3 cultures typically express PDX1.

"Pancreatic foregut precursor cells," as used herein, refers to cells that express at least one of the following markers: PDX1, NKX6.1, HNF6, NGN3, SOX9, PAX4, PAX6, ISL1, gastrin, FOXA2, PTF1α, PROX1 and HNF4α. Pancreatic foregut precursor cells may be characterized by being positive for the expression of PDX1, NKX6.1, and SOX9.

"Pancreatic endoderm cells," as used herein, refers to cells that express at least one of the following markers: PDX1, NKX6.1, HNF1 β, PTF1 α, HNF6, HNF4α, SOX9, NGN3; gastrin; HB9, or PROX1. Pancreatic endoderm cells may be characterized by their lack of substantial expression of CDX2 or SOX2.

"Pancreatic endocrine precursor cells," as used herein, refers to pancreatic endoderm cells capable of becoming a pancreatic hormone expressing cell. Pancreatic endocrine precursor cells express at least one of the following markers: NGN3; NKX2.2; NeuroD1; ISL1; PAX4; PAX6; or ARX. Pancreatic endocrine precursor cells may be characterized by their expression of NKX2.2 and NeuroD1.

"Pancreatic endocrine cells," as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NGN3, NeuroD1, ISL1, PDX1, NKX6.1, PAX4, ARX, NKX2.2, and PAX6. Pancreatic endocrine cells expressing markers characteristic of 13 cells can be characterized by their expression of insulin and at least one of the following transcription factors: PDX1, NKX2.2, NKX6.1, NeuroD1, ISL1, HNF3β, MAFA and PAX6.

Used interchangeably herein are "d1", "1 d", and "day 1"; "d2", "2 d", and "day 2", and so on. These number letter combinations refer to a specific day of incubation in the different stages during the stepwise differentiation protocol of the instant application.

"Glucose" is used herein to refer to dextrose, a sugar commonly found in nature.

"NeuroD1" is used herein to identify a protein expressed in pancreatic endocrine progenitor cells and the gene encoding it.

"LDN-193189" refers to ((6-(4-(2-(piperidin-1-yl) ethoxy)phenyl)-3-(pyridin-4-yl)pyrazolo[1,5-a]pyrimidine, hydrochloride; DM-3189)) a BMP receptor inhibitor available under the trademark STEMOLECULE™ from Stemgent, Inc., Cambridge, Mass., USA.

Characterization, Source, Expansion and Culture of Pluripotent Stem Cells

A. Characterization of Pluripotent Stem Cells

Pluripotent stem cells may express one or more of the stage-specific embryonic antigens (SSEA) 3 and 4, and markers detectable using Tra-1-60 and Tra-1-81 antibodies (Thomson et al. 1998, *Science* 282:1145-1147). Differentiation of pluripotent stem cells in vitro results in the loss of Tra-1-60, and Tra-1-81 expression. Undifferentiated pluripotent stem cells typically have Alkaline phosphatase activity, which can be detected by fixing the cells with 4% paraformaldehyde, and then developing with VECTOR® Red as a substrate, as described by the manufacturer (Vector Laboratories, CA, USA). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells may be confirmed, for example, by injecting cells into severe combined immunodeficiency ("SCID") mice, fixing the teratomas that form using 4% paraformaldehyde, and then histologically examining for evidence of cell types from these three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

B. Sources of Pluripotent Stem Cells

Exemplary types of pluripotent stem cells that may be used include established lines of pluripotent cells, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells or human embryonic germ cells, such as, for example the human embryonic stem cell lines H1, H7, and H9 (WiCell Research Institute, Madison, Wis., USA). Cells taken from a pluripotent stem cell population already cultured in the absence of feeder cells are also suitable. Inducible pluripotent cells (IPS), or reprogrammed pluripotent cells, derived from adult somatic cells using forced expression of a number of pluripotent related transcription factors, such as OCT4, NANOG, SOX2, KLF4, and ZFP42 (*Annu Rev Genomics Hum Genet* 2011, 12:165-185; see also IPS, *Cell,* 126(4): 663-676) may also be used. The human embryonic stem cells used in the methods of the invention may also be prepared as described by Thomson et al. (U.S. Pat. No. 5,843,780; *Science,* 1998, 282:1145-1147; *Curr Top Dev Biol* 1998, 38:133-165; *Proc Natl Acad Sci U.S.A.* 1995, 92:7844-7848). Mutant human embryonic stem cell lines, such as, BG01v (BresaGen, Athens, Ga.), or cells derived from adult human somatic cells, such as, cells disclosed in Takahashi et al., *Cell* 131: 1-12 (2007) may also be used. In certain embodiments, pluripotent stem cells suitable for use in the present invention may be derived according to the methods described in: Li et al. (*Cell Stem Cell* 4: 16-19, 2009); Maherali et al. (*Cell Stem Cell* 1: 55-70, 2007); Stadtfeld et al. (*Cell Stem Cell* 2: 230-240); Nakagawa et al. (*Nature Biotechnol* 26: 101-106, 2008); Takahashi et al. (*Cell* 131: 861-872, 2007); and U.S. Patent App. Pub. No. 2011/0104805. In certain embodiments, the pluripotent stem cells may be of non-embryonic origins. All of these references, patents, and patent applications are herein incorporated by reference in their entirety, in particular, as they pertain to the isolation, culture, expansion and differentiation of pluripotent cells.

C. Expansion and Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

Pluripotent cells may be readily expanded in culture using various feeder layers or by using matrix protein coated vessels. Alternatively, chemically defined surfaces in combination with defined media such as mTesr®1 media (StemCell Technologies, Vancouver, Canada) may be used for routine expansion of the cells. Pluripotent cells may be readily removed from culture plates using enzymatic digestive, mechanical separation, or various calcium chelators such as EDTA (ethylenediaminetetraacetic acid). Alternatively, pluripotent cells may be expanded in suspension in the absence of any matrix proteins or feeder layer.

Many different methods of expanding and culturing pluripotent stem cells may be used in the claimed invention. For example, the methods of the invention may use the methods of Reubinoff et al., Thompson et al., Richard et al. and U.S. Patent App. Pub. No. 2002/0072117. Reubinoff et al. (*Nature Biotechnology* 18: 399-404 (2000)) and Thompson et al. (*Science* 282: 1145-1147 (1998)) disclose the culture of pluripotent stem cell lines from human blastocysts using a mouse embryonic fibroblast feeder cell layer. Richards et al. (*Stem Cells* 21: 546-556, 2003) evaluated a panel of eleven different human adult, fetal, and neonatal feeder cell layers for their ability to support human pluripotent stem cell culture, noting that human embryonic stem cell lines cultured on adult skin fibroblast feeders retain human embryonic stem cell morphology and remain pluripotent. U.S. Patent App. Pub. No. 2002/0072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. U.S. Patent App. Pub. No. 2002/072117 also discloses the use of the cell lines as a primary feeder cell layer.

Other suitable methods of expanding and culturing pluripotent stem cells are disclosed, for example, in Wang et al., Stojkovic et al., Miyamoto et al. and Amit et al. Wang et al. (*Stem Cells* 23: 1221-1227, 2005) disclose methods for the long-term growth of human pluripotent stem cells on feeder cell layers derived from human embryonic stem cells. Stojkovic et al. (*Stem Cells* 2005 23: 306-314, 2005) disclose a feeder cell system derived from the spontaneous differentiation of human embryonic stem cells. Miyamoto et al. (*Stem Cells* 22: 433-440, 2004) disclose a source of feeder cells obtained from human placenta. Amit et al. (*Biol. Reprod* 68: 2150-2156, 2003) disclose a feeder cell layer derived from human foreskin.

In another embodiment, suitable methods of expanding and culturing pluripotent stem cells are disclosed, for example, in Inzunza et al., U.S. Pat. No. 6,642,048, WO 2005/014799, Xu et al. and U.S. Pub App. No 2007/0010011. Inzunza et al. (*Stem Cells* 23: 544-549, 2005) disclose a feeder cell layer from human postnatal foreskin fibroblasts. U.S. Pat. No. 6,642,048 discloses media that support the growth of primate pluripotent stem cells in feeder-free culture, and cell lines useful for production of such media. U.S. Pat. No. 6,642,048 reports mesenchymal and fibroblast-like cell lines obtained from embryonic tissue or differentiated from embryonic stem cells; as well as methods for deriving such cell lines, processing media and growing stem cells using such media. WO 2005/014799 discloses a conditioned medium for the maintenance, proliferation, and differentiation of mammalian cells. WO 2005/014799 reports that the culture medium produced via the disclosure is conditioned by the cell secretion activity of murine cells; in particular, those differentiated and immortalized transgenic hepatocytes, named MMH (Met Murine Hepatocyte). Xu et al. (*Stem Cells* 22: 972-980, 2004) discloses a conditioned medium obtained from human embryonic stem cell derivatives that have been genetically modified to over express human telomerase reverse transcriptase. U.S. Pub App. No 2007/0010011 discloses a chemically defined culture medium for the maintenance of pluripotent stem cells.

An alternative culture system employs serum-free medium supplemented with growth factors capable of promoting the proliferation of embryonic stem cells. Examples of such culture systems include, but are not limited, to Cheon et al., Levenstein et al. and U.S. Pub App. No. 2005/0148070. Cheon et al. (BioReprod DOI:10.1095/bioIreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal. Levenstein et al. (*Stem Cells* 24: 568-574, 2006) disclose methods for the long-term culture of human embryonic stem cells in the absence of fibroblasts or conditioned medium, using media supplemented with bFGF. U.S. Pub App. No. 2005/0148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

Other suitable methods of culturing and expanding pluripotent stem cells are disclosed in U.S. Patent App. Pub. No. 2005/0233446, U.S. Pat. No. 6,800,480, U.S. Patent App. Pub. No. 2005/0244962 and WO 2005/065354. U.S. Patent App. Pub. No. 2005/0233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells. U.S. Pat. No. 6,800,480 reports that a cell culture medium for growing primate-derived primordial stem cells in a substantially undifferentiated state is provided which includes a low osmotic pressure, low endotoxin basic medium that is effective to support the growth of primate-derived primordial stem cells. The disclosure of the U.S. Pat. No. 6,800,480 further reports that the basic medium is combined with a nutrient serum effective to support the growth of primate-derived primordial stem cells and a substrate selected from the group consisting of feeder cells and an extracellular matrix component derived from feeder cells. This medium is further noted to include non-essential amino acids, an antioxidant, and a first growth factor selected from the group consisting of nucleosides and a pyruvate salt. U.S. Patent App. Pub. No. 2005/0244962 reports that one aspect of the disclosure provides a method of culturing primate embryonic stem cells and that the stem cells in culture are essentially free of mammalian fetal serum (preferably also essentially free of any animal serum) and in the presence of fibroblast growth factor that is supplied from a source other than just a fibroblast feeder layer.

WO 2005/065354 discloses a defined, isotonic culture medium that is essentially feeder-free and serum-free, comprising: a basal medium; bFGF; insulin; and ascorbic acid. Furthermore, WO 2005/086845 discloses a method for maintenance of an undifferentiated stem cell, said method comprising exposing a stem cell to a member of the transforming growth factor-β (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as those derived from basement membrane or that may form part of adhesion molecule receptor-ligand couplings. In one embodiment, the suitable culture substrate is MATRIGEL™ (Becton Dickenson). MATRIGEL™ is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium, which promotes cell survival, propagation, and retention of the desirable characteristics. All these characteristics benefit from careful attention to the seeding distribution and can readily be determined by one of skill in the art. Suitable culture media may be made, for example, from the following components: Dulbecco's modified Eagle's medium (DMEM), sold under the trademark Gibco™ (part #11965-092) by Life Technologies Corporation, Grand Island, N.Y.; Knockout Dulbecco's modified Eagle's medium (KO DMEM), sold under the trademark Gibco™ (part #10829-018) by Life Technologies Corporation, Grand Island, N.Y.; Ham's F12/50% DMEM basal medium; 200 mM L-glutamine, sold under the trademark Gibco™ (part #15039-027) by Life Technologies Corporation, Grand Island, N.Y.; non-essential amino acid solution, sold under the trademark Gibco™ (part #11140-050) by Life Technologies Corporation, Grand Island, N.Y.; β-mercaptoethanol, (part #M7522) sold by Sigma-Aldrich, Company, LLC, Saint Louis, Mo.; and human recombinant basic fibroblast growth factor (bFGF), sold under the trademark Gibco™ (part #13256-029) by Life Technologies Corporation, Grand Island, N.Y.

Differentiation of Pluripotent Stem Cells

As pluripotent cells differentiate towards β cells, they differentiate through various stages each of which may be characterized by the presence or absence of particular markers. Differentiation of the cells into these stages is achieved by the specific culturing conditions including the presence or lack of certain factors added to the culture media. In general, this differentiation may involve differentiation of pluripotent stem cells into definitive endoderm cells. These definitive endoderm cells may then be further differentiated into gut tube cells, which in turn may then be differentiated into foregut endoderm cells. Foregut endoderm cells may be differentiated into pancreatic foregut precursor cells which can, in turn, differentiate into pancreatic endoderm cells, pancreatic endocrine precursor cells or both. These cells may then be differentiated into pancreatic hormone producing cells (such as β cells).

This invention provides for staged differentiation of pluripotent stem cells toward pancreatic endocrine cells using a thyroid hormone (such as T3, analogues of T3, T4, analogues of T4 or combinations thereof (collectively referred to hereinafter as "T3/T4")) and an ALK5 inhibitor. This invention also provides for staged differentiation of pluripotent stem cells toward pancreatic endocrine cells using a thyroid hormone (such as T3/T4) or an ALK5 inhibitor. Suitable thyroid hormone analogues may include: GC-1 (Sobertirome) available from R & D Systems, Inc. Catalogue #4554; DITPA (3,5-diiodothyropropionic acid); KB-141, discussed in *J. Steroid Biochem. Mol. Biol.* 2008, 111: 262-267 and *Proc. Natl. Acad. Sci. US* 2003, 100: 10067-10072; MB07344, discussed in *Proc. Natl. Acad. Sci. US* 2007, 104: 15490-15495; T0681, discussed in *PLoS One*, 2010, 5e8722 and *J. Lipid Res.* 2009, 50: 938-944; and GC-24, discussed in *PLoS One,* 2010 e8722 and *Endocr. Pract.* 2012, 18(6): 954-964, the disclosures of which are incorporated herein in their entirety. Useful ALK5 inhibitors include: ALK5 inhibitor II (Enzo, Farmingdale, N.Y.); ALK5i (Axxora, San Diego, Calif.); SD208 (R & D systems (MN)); TGF-B inhibitor SB431542 (Xcess Biosciences (San Diego, Calif.)); ITD-1 (Xcess Biosciences (San Diego, Calif.)); LY2109761 (Xcess Biosciences (San Diego, Calif.)); A83-01 (Xcess Biosciences (San Diego, Calif.)); LY2157299 (Xcess Biosciences (San Diego, Calif.)); TGF-β receptor inh V (EMD Chemicals, Gibstown, N.J.); TGF-β receptor inh I (EMD Chemicals, Gibstown, N.J.); TGF-β receptor inh IV (EMD Chemicals, Gibstown, N.J.); TGF-β receptor inh VII (EMD Chemicals, Gibstown, N.J.); TGF-β receptor inh VIII (EMD Chemicals, Gibstown, N.J.); TGF-β receptor inh II (EMD Chemicals, Gibstown, N.J.); TGF-β receptor inh VI (EMD Chemicals, Gibstown, N.J.); TGF-β receptor inh III (EMD Chemicals, Gibstown, N.J.).

Differentiation of Pluripotent Stem Cells into Cells Expressing Markers Characteristic of Pancreatic Endocrine Cells Characteristics of pluripotent stem cells are well known to those skilled in the art, and additional characteristics of pluripotent stem cells continue to be identified. Pluripotent stem cell markers include, for example, the expression of one or more of the following: ABCG2; cripto; FOXD3; CONNEXIN43; CONNEXIN45; OCT4; SOX2; NANOG; hTERT; UTF1; ZFP42; SSEA-3; SSEA-4; TRA-1-60; and TRA-1-81.

Exemplary pluripotent stem cells include the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, TRA-1-60, and TRA-1-81.

Also suitable for use in the present invention is a cell that expresses at least one of the markers characteristic of the definitive endoderm lineage. In one embodiment of the invention, a cell expressing markers characteristic of the definitive endoderm lineage is a primitive streak precursor cell. In an alternate embodiment, a cell expressing markers characteristic of the definitive endoderm lineage is a mesendoderm cell. In an alternate embodiment, a cell expressing markers characteristic of the definitive endoderm lineage is a definitive endoderm cell.

Also suitable for use in the present invention is a cell that expresses at least one of the markers characteristic of the pancreatic endoderm lineage. In one embodiment of the present invention, a cell expressing markers characteristic of the pancreatic endoderm lineage is a pancreatic endoderm cell in which the expression of PDX1 and NKX6.1 are substantially higher than the expression of CDX2 and SOX2. Particularly useful are cells in which the expression of PDX1 and NKX6.1 is at least two-fold higher than the expression of CDX2 or SOX2.

In one embodiment, pancreatic endocrine cells capable of expressing at least one of the following hormones: insulin, glucagon, somatostatin, and pancreatic polypeptide are generated. Suitable for use in the present invention is a precursor cell that expresses at least one of the markers characteristic of the pancreatic endocrine lineage. In one embodiment of the present invention, a cell expressing markers characteristic of the pancreatic endocrine lineage is a pancreatic endocrine cell. In a preferred embodiment, the pancreatic endocrine cell is an insulin-producing β cell.

In certain embodiments of the invention, to arrive at the cells expressing markers characteristic of pancreatic endocrine cells, a protocol starting with pluripotent stem cells or inducible pluripotent cells, preferably pluripotent stem cells, is employed. This protocol includes the following stages.

Stage 1: Pluripotent stem cells, such as embryonic stem cells obtained for cell culture lines, are treated with appropriate factors to induce differentiation into cells expressing markers characteristic of definitive endoderm cells.

Stage 2: Cells resulting from Stage 1 are treated with appropriate factors to induce further differentiation into cells expressing markers characteristic of gut tube cells.

Stage 3: Cells resulting from Stage 2 are treated with appropriate factors to induce further differentiation into cells expressing markers characteristic of foregut endoderm cells.

Stage 4: Cells resulting from Stage 3 are treated with appropriate factors (including in certain embodiments T3/T4) to induce further differentiation into cells expressing markers characteristic of pancreatic foregut precursor cells.

Stage 5: Cells resulting from Stage 4 are treated with appropriate factors (including in certain embodiments: (i) T3/T4; (ii) an ALK5 inhibitor; or (iii) both T3/T4 and an ALK 5 inhibitor) to induce further differentiation into cells expressing markers characteristic of pancreatic endoderm/endocrine precursor cells.

Stage 6: Cells resulting from Stage 5 are treated with appropriate factors (including in certain embodiments T3/T4, an ALK5 inhibitor, or both) to induce further differentiation into cells expressing markers characteristic of pancreatic endocrine cells.

While the invention, in certain embodiments, encompasses differentiating pluripotent stem cells to cells expressing markers characteristic of pancreatic endocrine cells, the invention also encompasses differentiating cells resulting from other intermediate stages towards pancreatic endocrine cells. In particular, the invention encompasses differentiation of cells expressing markers characteristic of pancreatic foregut precursor cells into cells expressing markers characteristic of pancreatic endocrine cells. Moreover, although the process is described in discrete stages, the treatment, as well as the progress of the cells through the differentiation process, may be sequential or continuous.

Methods for assessing expression of protein and nucleic acid markers in cultured or isolated cells are standard in the art. These methods include RT-PCR, Northern blots, in situ hybridization (see, e.g., Current Protocols in Molecular Biology (Ausubel et al., eds. 2001 supplement)), and immunoassays (such as immunohistochemical analysis of sectioned material), Western blotting, and for markers that are accessible in intact cells, FACS (see, e.g., Harlow and Lane, Using Antibodies: A Laboratory Manual, New York: Cold Spring Harbor Laboratory Press (1998)). Further, the efficiency of differentiation may be determined by exposing a treated cell population to an agent (such as an antibody) that specifically recognizes a protein marker expressed by cells expressing markers characteristic of the cell type of interest.

The differentiated cells may also be further purified. For example, after treating pluripotent stem cells with the methods of the present invention, the differentiated cells may be purified by exposing a treated cell population to an agent (such as an antibody) that specifically recognizes a protein marker characteristically expressed by the differentiated cells being purified.

Stage 1: Differentiation of pluripotent stem cells into cells expressing markers characteristic of definitive endoderm cells Pluripotent stem cells may be differentiated into cells expressing markers characteristic of definitive endoderm cells by any suitable method known in the art, or by any method proposed in this invention. Suitable methods of differentiating pluripotent stem cells into cells expressing markers characteristic of definitive endoderm cells are disclosed in: U.S. Patent App. Pub. No. 2007/0254359; U.S. Patent App. Pub. No. 2009/0170198; U.S. Patent App. Pub. No. 2009/0170198; U.S. Patent App. Pub. No. 2011/0091971; U.S. Patent App. Pub. No. 2010/0015711; U.S. Patent App. Pub. No. 2010/0015711; U.S. Patent App. Pub. No. 2012/0190111; U.S. Patent App. Pub. No. 2012/0190112; U.S. Patent App. Pub. No. 2012/0196365; U.S. Patent App. Pub. No. 20100015711; U.S. Patent App. Pub. No. 2012/0190111; U.S. Patent App. Pub. No. 2012/0190112; U.S. Patent App. Pub. No. 2012/0196365; U.S. Patent App. Pub. No. 20100015711; U.S. Patent App. Pub. No. 2012/0190111; U.S. Patent App. Pub. No. 2012/0190112; U.S. Patent App. Pub. No. 2012/0196365; U.S. Provisional Patent Application No. 61/076,900; U.S. Provisional Patent Application No. 61/076,908; and U.S. Provisional Patent Application No. 61/076,915, which are incorporated by reference in their entireties as they relate to pluripotent stem cells and to the differentiation of pluripotent stem cells into cells expressing markers characteristic of definitive endoderm cells.

In one embodiment of the invention, pluripotent stem cells are treated with a medium supplemented with activin A and Wnt3A to result in the generation of cells expressing markers characteristic of definitive endoderm cells. Treatment may involve contacting pluripotent stem cells with a medium containing about 50 ng/ml to about 150 ng/ml, alternatively about 75 ng/ml to about 125 ng/ml, alternatively about 100 ng/ml of activin A. The treatment may also involve contacting the cells with about 10 ng/ml to about 50 ng/ml, alternatively about 15 ng/ml to about 30 ng/ml, alternatively about 20 ng/ml of Wnt3A. The pluripotent cells may be cultured for approximately two to five days, preferably about two to three days, to facilitate their differentiation into cells expressing markers characteristic of definitive endoderm cells. In one embodiment, the pluripotent cells are cultured in the presence of activin A and Wnt3A for one day, followed by culturing in the presence of activin A (without Wnt3A being present).

In another embodiment of the invention, pluripotent stem cells are treated with a medium supplemented with growth differentiation factor 8 ("GDF8") and a glycogen synthase kinase-3 β ("GSK3β") inhibitor (such as the cyclic anilinepyridinotriazine compounds disclosed in U.S. Patent App. Pub. No. 2010/0015711; incorporated herein by reference in its entirety) to induce differentiation into cells expressing markers characteristic of definitive endoderm cells. A preferred GSK30 inhibitor is (14-Prop-2-en-1-yl-3,5,7,14,17,23,27-heptaazatetracyclo [19.3.1.1~2,6~0.1~8,12~]heptacosa-1(25),2(27),3,5,8(26),9,11,21,23-nonaen-16-one, referred to herein as "MCX Compound". Treatment may involve contacting pluripotent stem cells with a medium supplemented with about 50 ng/ml to about 150 ng/ml, alternatively about 75 ng/ml to about 125 ng/ml, alternatively about 100 ng/ml of GDF8. The treatment may also involve contacting the cells with about 0.1 to 5 alternatively about 0.5 to about 2.5 preferable about 1 µM of MCX compound. The pluripotent cells may be cultured for approximately two to five days, preferably about three to four days, to facilitate their differentiation into definitive endoderm cells. In one embodiment, the pluripotent cells are cultured in the presence of GDF8 and MCX compound for one day, followed by culturing in the presence of GDF8 and a lower concentration of MCX compound for one day, followed by culturing in the presence of GDF8 for one day in the absence of the MCX compound. In particular, the cells may be cultured in the presence of GDF8 and about 1 µM of MCX compound for one day, followed by culturing in the presence of GDF8 and about 0.1 µM MCX compound for one day, followed by culturing in the presence of GDF8 for one day in the absence of the MCX compound. In an alternate embodiment, the cells may be cultured in the presence of GDF8 and about 1 µM of MCX compound for one day, followed by culturing in the presence of GDF8 and about 0.1 µM MCX compound for one day.

Generation of cells expressing markers characteristic of definitive endoderm cells may be determined by testing for the presence of the markers before and after following a particular protocol. Pluripotent stem cells typically do not express such markers. Thus, differentiation of pluripotent cells can be detected when the cells begin to express markers characteristic of definitive endoderm cells.

Stage 2: Differentiation of cells expressing markers characteristic of definitive endoderm cells into cells expressing markers characteristic of gut tube cells The cells expressing markers characteristic of definitive endoderm cells may be further differentiated into cells expressing markers characteristic of gut tube cells. In one embodiment, the formation of cells expressing markers characteristic of gut tube cells includes culturing cells expressing markers characteristic of definitive endoderm cells with a medium containing fibroblast growth factor ("FGF")7 or FGF10 to differentiate these cells. For example, the culture medium may include from about 25 ng/ml to about 75 ng/ml, alternatively from about 30 ng/ml to about 60 ng/ml, alternatively about 50 ng/ml of FGF7 or FGF10, preferably FGF7. The cells may be cultured under these conditions for about two to three days, preferably about two days.

In another embodiment, differentiation into cells expressing markers characteristic of gut tube cells includes culturing cells expressing markers characteristic of definitive endoderm cells with FGF7 or FGF10, and ascorbic acid (vitamin C). The culture medium may include from about 0.1 mM to about 0.5 mM ascorbic acid, alternatively from about 0.2 mM to about 0.4 mM, alternatively about 0.25 mM of ascorbic acid. The culture medium may also include from about 10 ng/ml to about 35 ng/ml, alternatively from about 15 ng/ml to about 30 ng/ml, alternatively about 25 ng/ml of FGF7 or FGF10, preferably FGF7. For example, the culture medium may include about 0.25 mM of ascorbic acid and about 25 ng/ml of FGF-7. In one embodiment, cells expressing markers characteristic of definitive endoderm cells are treated for 2 days with FGF7 and ascorbic acid.

Stage 3: Differentiation of cells expressing markers characteristic of gut tube cells into cells expressing markers characteristic of foregut endoderm cells Cells expressing markers characteristic of gut tube cells may be further differentiated into cells expressing markers characteristic of foregut endoderm cells. In one embodiment, Stage 2 cells are further differentiated into Stage 3 cells by culturing these cells in a culture medium supplemented with a Smoothened ("SMO") receptor inhibitor (such as cyclopamine or MRT10 (N-[[[3-benzoylamino) phenyl]amino]thioxomethyl]-3,4,5-trimethoxybenzamide)) or a Sonic Hedgehog ("SHH") signaling pathway antogonist (such as Smoothened Antogonist 1 ("SANT-1") ((E)-4-benzyl-N-((3,5-dimethyl-1-phenyl-1H-pyrazol-4-yl) methylene-piperazin-1-amine)), Hedgehog Pathway Inhibitor 1 ("HPI-1") (2-methoxyethyl 1,4,5,6,7,8-hexahydro-4-(3-hydroxyphenyl)-7-(2-methoxyphenyl)-2-methyl-5-oxo-3-quinolinecarboxylate), retinoic acid and Noggin. Alternatively, the medium may be supplemented with a SMO inhibitor, SHH signaling pathway antagonist, retinoic acid and Noggin. The cells may be cultured for approximately two to four days, preferably about two days. In one embodiment, the medium is supplemented with from about 0.1 μM to about 0.3 μM of SANT-1, from about 0.5 μM to about 3 μM of retinoic acid and from about 75 ng/ml to about 125 ng/ml of Noggin. In another embodiment, the medium is supplemented with about 0.25 μM of SANT-1, about 2 μM of retinoic acid and about 100 ng/ml of Noggin.

In an alternate embodiment, Stage 2 cells are further differentiated into Stage 3 cells by treating the Stage 2 cells with a medium supplemented with FGF7 or FGF10, retinoic acid, a SMO inhibitor (such as MRT10 or cyclopamine) or SHH signaling pathway antagonist (such as SANT-1 or HPI-1), a protein Kinase C ("PKC") activator (such as ((2S,5S)-(E,E)-8-(5-(4-(Trifluoromethyl)phenyl)-2,4-pentadienoylamino)benzolactam) ("TPB"); EMD Chemicals Inc., Gibbstown N.J.), phorbol-12,13-dibutyrate ("PDBu"), phorbol-12-myristate-13-acetate ("PMA") or indolactam V ("ILV"), a bone morphogenic protein ("BMP") inhibitor (such as LDN-193189, Noggin or Chordin), and ascorbic acid. In another embodiment, the medium may be supplemented with FGF7 or FGF10, retinoic acid, a SMO inhibitor, a SHH signaling pathway antagonist (such as SANT-1), a PKC activator (such as TPB), a BMP inhibitor (such as LDN-193189), and ascorbic acid. The cells may be cultured in the presence of these growth factors, small molecule agonists, and antagonists for about two to three days.

In one embodiment, the medium is supplemented with from about 15 ng/ml to about 35 ng/ml of FGF7, from about 0.5 μM to about 2 μM of retinoic acid, from about 0.1 μM to about 0.4 μM of SANT-1, from about 100 nM to about 300 nM of TPB, from about 50 nM to about 200 nM of LDN-193189, and from about 0.15 mM to about 0.35 mM of ascorbic acid. In another embodiment, the medium is supplemented with about 25 ng/ml of FGF7, about 1 μM of retinoic acid, about 0.25 μM of SANT-1, about 200 nM of TPB, about 100 nM of LDN-193189, and about 0.25 mM of ascorbic acid.

Stages 4 to 6: Differentiation of cells expressing markers characteristic of foregut endoderm cells into cells expressing markers characteristic of pancreatic endoderm cells by treatment with culture media supplemented with thyroid hormones T3/T4 or ALK5 inhibitor, or both T3/T4 and ALK5 inhibitor.

This invention provides for the further differentiation of cells expressing markers characteristic of foregut endoderm cells by treatment with culture media supplemented with thyroid hormone T3/T4, or an ALK5 inhibitor, or both T3/T4 and an ALK5 inhibitor. In some embodiments, the invention provides for further differentiation of such cells in Stage 4 to Stage 6 by treatment with culture media supplemented with (a) T3, (b) an ALK5 inhibitor or (c) T3 and an ALK5 inhibitor at one or more of these stages.

In one embodiment, the present invention provides a method for producing cells expressing markers characteristic of pancreatic endocrine cells from pluripotent stem cells comprising:

a. culturing pluripotent stem cells;
b. differentiating the pluripotent stem cells into cells expressing markers characteristic of foregut endoderm cells; and
c. differentiating the cells expressing markers characteristic of foregut endoderm cells into cells expressing markers characteristic of pancreatic endocrine cells by treatment with a medium supplemented with (i) T3/T4, (ii) an ALK5 inhibitor, or (iii) both T3/T4 and an ALK5 inhibitor.

In one embodiment, the cells expressing markers characteristic of pancreatic endocrine cells are β cells. In another embodiment, the resulting cells are positive for NKX6.1, PDX1, and HB-9. The method may enhance the number of HB9 positive cells in NKX6.1 positive pancreatic endoderm precursor cells. The method may also decrease expression of NKX2.2 or SOX2, or both, as well as albumin expression. The method may also provide cells expressing markers characteristic of pancreatic endocrine cells, including β cells, by culturing cells expressing markers characteristic of pancreatic endoderm/endocrine cells in a medium supplemented with T3/T4. The methods of producing cells expressing markers characteristic of pancreatic endocrine cells from pluripotent stem cells may employ the culture conditions shown in the Tables I to III, or described herein. In one embodiment, the ALK 5 inhibitor is SD208 (2-(5-Chloro-2-fluorophenyl)pteridin-4-yl]pyridin-4-yl-amine). In another embodiment, ALK5 inhibitor II ((2-(3-(6-Methylpyridin-2-yl)-1H-pyrazol-4-yl)-1,5-naphthyridine), ALX-270-445, ENZO, Farmingdale, N.Y.) can also be used.

Treatment of cells in Stages 4 to 6 with culture media supplemented with T3/T4, an ALK5 inhibitor, or both provides for several advantages. For example, the addition of the thyroid hormones at Stage 4 to Stage 6 significantly downregulates glucagon, somatostatin, and ghrelin while moderately increasing insulin expression at Stage 5. The addition of T3/T4 at Stages 4 to 6 also appears to significantly decrease expression of NKX2.2 while not impacting NKX6.1 and PDX1 expression. Furthermore, T3/T4 addition at Stages 4 to 6 suppresses SOX2 (stomach marker) and albumin (liver marker) expression while not affecting CDX2 (intestine marker) expression. Moreover, compared to an untreated control, treatment with T3 at Stage 4 increases the number of HB9 positive cells at Stage 6. Furthermore, T3 treatment resulted in an increased number of NKX6.1 positive cells that express HB9. Prolonged exposure to both an ALK5 inhibitor and T3/T4 appears to significantly enhance expression of HB9 while maintaining robust expression of NKX6.1. The inclusion of T3/T4 in a culture medium, appears, in a dose dependent manner, to significantly enhance the number of HB9 positive cells in the NKX6.1 positive pancreatic endoderm precursor cells.

Accordingly, in certain embodiments, the invention provides for methods of down-regulating glucagon, somatostatin and ghrelin in the differentiated cells provided in Stage 4 to Stage 6 by treatment with a medium supplemented with at least thyroid hormones T3/T4. Moreover, the invention also provides for methods of decreasing NKX 2.2 expression in the differentiated cells provided in Stage 4 to Stage 6 that express NKX6.1 and PDX1 by treatment with a medium supplemented with at least thyroid hormones T3/T4. In addition, the invention provides methods for increasing NKX6.1 positive cells expressing HB9 by culturing in a medium with thyroid hormones T3/T4 and optionally an ALK5 inhibitor. In certain embodiments, the methods use the culture conditions shown in Tables I-III.

One embodiment of the invention is a method of forming cells expressing markers characteristic of β cells comprising differentiating cells expressing markers characteristic of the foregut endoderm into cells expressing markers characteristic of β cells by treatment with media supplemented with thyroid hormones T3/T4, an ALK5 inhibitor, or both (such as T3 and an ALK5 inhibitor). The resulting cells are positive for NKX6.1, PDX1, and Hb-9. The method may be used to enhance the number of HB9 positive cells in NKX6.1 positive pancreatic endoderm precursor cells. The method may also be used to decrease expression of NKX2.2. Additionally, the method may be used to suppress SOX2 and albumin expression. The thyroid hormone may be T3. The method may also be used to enhance HB9 expression when compared to cells that are not cultured with a medium supplemented with T3 and an ALK5 inhibitor. Furthermore, the method comprises formation of cells expressing markers characteristic of β cells by culturing cells expressing cells markers characteristic of pancreatic endoderm/endocrine precursor cells in a medium supplemented with T3/T4. The method may employ the culture conditions shown in Tables I-III or described herein.

Yet another embodiment of the invention is a method of down-regulating glucagon, somatostatin and ghrelin in cells expressing markers characteristic of pancreatic foregut precursor cells, cells expressing markers characteristic of pancreatic endoderm/endocrine precursor cells or cells expressing markers characteristic of pancreatic endocrine cells by culturing the cells in a medium supplemented with T3/T4 and an ALK5 inhibitor. The medium may be further supplemented with a SMO inhibitor, a SHH signaling pathway antagonist (such as SANT-1), retinoic acid, and ascorbic acid. Alternatively, the medium may be further supplemented with a SMO inhibitor or a SHH signaling pathway antagonist, retinoic acid, and ascorbic acid. The medium, especially when used at Stage 4, may preferably be supplemented with FGF7. In certain embodiments, the method employs the culture conditions shown in Tables I-III or described herein.

Specifically, in certain embodiments, the cells may be treated in Stage 4 to Stage 6 (i.e. in Stage 4 and Stage 5 and Stage 6, or in Stage 4 and Stage 5, or in Stage 5 and Stage 6, or in Stage 4 and Stage 6) as outlined in Table I below, which shows exemplary culture conditions suitable for use in the methods of the invention. In certain embodiments, any one of the treatments at one stage (e.g. Stage 4) may be combined with any one of the treatments at another stage (e.g. Stage 5).

In an alternate embodiment, the present invention provides an in vitro cell culture for differentiating cells derived from pluripotent stem cells into cells expressing markers characteristic of pancreatic endocrine β cells, as well as PDX1, NKX6.1 and HB9. The cell culture comprises a culture vessel, differentiation medium, and a population of differentiated cells derived from pluripotent stem cells. The cell culture provides a population of differentiated cells wherein at least ten percent of the differentiated cells express PDX1, NKX6.1 and HB9. Media useful in the cell culture are set forth in Tables I-III, and preferably contain T3/T4, or an ALK5 inhibitor or both

TABLE I

Exemplary Culture Conditions suitable for use in the methods of the invention

| | Stage 4 | Stage 5 | Stage 6 |
|---|---|---|---|
| Treatment of with at least | Stage 3 cells<br>T3<br>T3<br>T3 | Stage 4 cells<br>ALK5 inhibitor + T3<br>ALK5 inhibitor + T3<br>T3 | Stage 5 cells<br>T3<br>ALK5 inhibitor + T3<br>T3 |
| Other optional components | One or more of:<br>SANT-1<br>Retinoic Acid<br>Ascorbic Acid<br>FGF7<br>BMP Receptor Inhibitor (e.g. LDN-193189)<br>PKC activator (e.g. TPB) | One or more of:<br>SANT-1<br>Retinoic Acid<br>Ascorbic Acid | One or more of:<br>SANT-1<br>Retinoic Acid<br>Ascorbic Acid |
| Duration of Treatment | Approximately 2-4 days, preferably about 3 days | Approximately 2-4 days, preferably about 3 days | Approximately 2-4 days, preferably about 3 days |

While T3 is generally preferred, other thyroid hormones may be used in place of T3. In particular, T4 may be used in place of T3 as well as suitable analogs of T3 and T4. Suitable thyroid hormone analogues may include: GC-1 (Sobertirome) available from R & D Systems, Inc. Catalogue #4554; DITPA (3,5-diiodothyropropionic acid); KB-141, discussed in J. Steroid Biochem. Mol. Biol. 2008, 111: 262-267 and Proc. Natl. Acad. Sci. US 2003, 100: 10067-10072; MB07344, discussed in Proc. Natl. Acad. Sci. US 2007, 104: 15490-15495; T0681, discussed in PLoS One, 2010, 5e8722 and J. Lipid Res. 2009, 50: 938-944; and GC-24, discussed in PLoS One, 2010 e8722 and Endocr. Pract. 2012, 18(6): 954-964, the disclosures of which are incorporated herein in their entirety. The amounts of T3, ALK5 inhibitor, SANT-1, Retinoic Acid, Ascorbic Acid, FGF7, LDN-193189, and TPB may vary in each stage. Exemplary suitable ranges of these components are shown below in Table II.

TABLE II

Exemplary amounts of culture components suitable for use in the methods of the invention

| Component | Exemplary Suitable Amount | Alternatively |
|---|---|---|
| T3 | about 0-1,000 nM | About 1 to about 1000 nM, about 10 to about 900 nM, about 100 to about 800 nM, about 200 to about 700 nM, about 300 to about 600 nM, about 400 to about 500 nM, about 1 to about 500 nM, about 1 to about 100 nM, about 100 to about 1000 nM, about 500 to about 1000 nM, about 100 nM, about 500 nM, or about 1 μM |
| ALK5 inhibitor | about to 250 nM to about 2 μM | About 300 to about 2000 nM, about 400 to about 2000 nM, about 500 to about 2000 nM, about 600 to about 2000 nM, about 700 to about 2000 nM, about 800 to about 2000 nM, about 1000 to about 2000 nM, about 1500 to about 2000 nM, about 250 to about 1000 nM, about 250 to about 500 nM, about 300 to about 1000 nM, about 400 to about 1000 nM, about 500 to about 1000 nM, about 600 to about 1000 nM, about 700 to about 1000 nM, about 800 to about 1000 nM, about 100 nM, about 500 nM or about 1 μM |
| SANT-1 | from about 0.1 μM to about 0.3 μM | about 0.25 μM |
| Retinoic Acid | From about 100-2000 nM for stage 3 from about 25 nM to about 150 nM for stages 4, 5, and 6 | From about 200-1800, about 300-1700, about 400-1500, about 500-1500, about 500-1000 nM for stage 3 about 25nM to about 100 nM, about 50 nM to about 150 nM, about 50 nM to about 100 nM, about 25 nM, about 50 nM, or about 100 nM for stages 4, 5, and 6 |
| Ascorbic Acid | from about 0.1 to about 0.4 mM | About 0.1 to about 0.3 mM, about 0.1 to about 0.25 mM, about 0.1 to about 0.2 mM, about 0.1 to about 0.15 mM, about 0.15 to about 0.4 mM, about 0.2 to about 0.4 mM, about 0.25 to about 0.4 mM, about 0.3 to about 0.4 mM, about 0.1 mM, about 0.2 mM, about 0.3mM, about 0.4 mM or about 0.25 mM |
| FGF7 | From about 2 to about 35 ng/ml | About 2 to about 30 ng/ml, about 5 to about 25 ng/ml, about 10 to about 20 ng/ml, about 2 to about 25 ng/ml, about 2 to about 20 ng/ml, about 2 to about 15 ng/ml, about 2 to about 10 ng/ml, about 2 to about 5 ng/ml, about 5 to about 35 ng/ml, about 10 to about 35 ng/ml, about 15 to about 35 ng/ml, about 20 to about 35 ng/ml, about 25 to about 35 ng/ml, about 30 to about 35 ng/ml, about 2 ng/ml, about 5 ng/ml, about 10 ng/ml, about 15 ng/ml, about 20 ng/ml about 25 ng/ml, about 30 ng/ml or about 35 ng/ml |
| BMP Receptor Inhibitor (e.g. LDN) | From about 50 to about 150 mM | About 50 to about 140 nM, about 50 to about 130 nM, about 50 to about 120 nM, about 50 to about 110 nM, about 50 to about 100 nM, about 50 to about 90 nM, about 50 to about 80 nM, about 60 to about 150 nM, about 70 to about 150 nM, about 80 to about 150 nM, about 90 to about 150 nM, about 100 to about 150 nM, about 80 to about 120 nM, about 90 to about 110 nM, about 50 nM, about 100 nM, or about 150 nM. |
| PKC activator (e.g. TPB) | From about 50 to about 150 mM | About 50 to about 140 nM, about 50 to about 130 nM, about 50 to about 120 nM, about 50 to about 110 nM, about 50 to about 100 nM, about 50 to about 90 nM, about 50 to about 80 nM, about 60 to about 150 nM, about 70 to about 150 nM, about 80 to about 150 nM, about 90 to about 150 nM, about 100 to about |

TABLE II-continued

Exemplary amounts of culture components suitable for use in the methods of the invention

| Component | Exemplary Suitable Amount | Alternatively |
|---|---|---|
| | | 150 nM, about 80 to about 120 nM, about 90 to about 110 nM, about 50 nM, about 100 nM, or about 150 nM. |

In one embodiment, the methods of the invention include treating cells expressing markers characteristic of foregut endoderm cells with a medium supplemented with SANT-1, retinoic acid ("RA"), FGF7, LDN-193189, ascorbic acid, and TPB for about two to four days, preferably about three days, to differentiate them into cells expressing markers characteristic of pancreatic foregut precursor cells. In particular, Stage 3 cells may be treated with a medium supplemented with about 0.25 µM SANT-1; about 100 nM RA; about 2 ng/ml FGF7; about 100 nM LDN-193189; and about 0.25 mM ascorbic acid; and about 100 nM TPB for three days. In one embodiment, the medium is further supplemented with T3, such as about 1 µM of T3. In another embodiment, the medium may be supplemented with an ALK5 inhibitor such as about 1 µM of ALK5 inhibitor.

In an alternate embodiment, the methods of the invention include treating cells expressing markers characteristic of pancreatic foregut precursor cells with a medium supplemented with SANT-1, RA, ascorbic acid, and an ALK5 inhibitor for about two to three days to differentiate the cells into cells expressing markers characteristic of pancreatic endoderm/endocrine precursor cells. In certain embodiments, the medium may be further supplemented with T3. In one embodiment, Stage 4 cells are differentiated into Stage 5 cells by treating the cells with a medium supplemented with about 0.25 µM SANT-1, about 50 nM RA, about 0.25 mM ascorbic acid, and about 500 nM ALK5 inhibitor. In another embodiment, the Stage 4 cells are further differentiated into Stage 5 cells by treating the cells with a medium supplemented with about 0.25 µM SANT-1, about 50 nM RA, about 0.25 mM ascorbic acid, about 1 µM ALK5 inhibitor and 0-1000 (e.g. 100) nM T3/T4 for about two to four days, preferably about three days. In one embodiment, Stage 4 cells derived according to embodiments of the invention are utilized and differentiated into Stage 5 cells, while in other embodiments Stage 4 cells derived according to other protocols may be utilized.

In one embodiment of the invention, cells expressing markers characteristic of pancreatic endoderm/endocrine precursor cells are differentiated into cells expressing markers characteristic of pancreatic endocrine cells by treating them with a medium supplemented with SANT-1, RA, ascorbic acid and either (1) T3/T4 or (2) T3/T4 and ALK5 inhibitor for about two to four days, preferably about three days. For example, Stage 5 cells may be differentiated into Stage 6 cells by treatment with a medium supplemented with about 0.25 µM SANT-1, about 50 nM RA, about 0.25 mM ascorbic acid and about 1 µM of T3/T4 for about three days. Alternatively, Stage 5 cells may be differentiated into Stage 6 cells by treatment with a medium supplemented with about 0.25 µM SANT-1, about 50 nM RA, about 0.25 mM ascorbic acid, about 500 nM ALK5 inhibitor and 10 nM T3/T4 for about three days. Alternatively, Stage 5 cells may be differentiated into Stage 6 cells by treatment with a medium supplemented with about 0.25 µM SANT-1, about 50 nM RA, about 0.25 mM ascorbic acid, about 1 µM of ALK5 inhibitor and 0-1000 nM T3/T4 for about three days. The cells may be further cultured in such media as desired, for example, for a total of about 15 days.

In one embodiment, Stage 5 cells derived according to embodiments of the invention are utilized and differentiated into Stage 6 cells, while in other embodiments Stage 5 cells derived according to other protocols may be utilized.

One aspect of the invention provides methods of enhancing expression of HB9 by treating Stage 4 to Stage 6 cells in a medium comprising T3/T4 or an ALK5 inhibitor or combinations thereof. The Stage 4, Stage 5 and Stage 6 cells may be pancreatic foregut precursor cells, pancreatic endoderm/endocrine precursor cells, and pancreatic endocrine cells, respectively. In some embodiments, the treated population of cells expresses at least two times as much HB9 protein as non-treated cultures. In other embodiments, the level of expression of insulin is positively affected in treated cultures as compared to untreated cultures. However, expression of somatostatin, ghrelin, and glucagon is decreased in treated vs. non-treated cultures. In additional embodiments, Stage 5 cells do not substantially express CDX2 or SOX2.

In further embodiments, the present invention relates to a stepwise method of differentiating pluripotent cells comprising culturing Stage 4 to Stage 6 cells in a media comprising sufficient amounts of T3/T4 or ALK5 inhibitor, or combinations thereof, to generate a population of pancreatic endoderm lineage cells positive for NKX6.1, PDX1, and HB9 protein. In other embodiments, at least 5% of PDX1 and NKX6.1 co-positive cells express HB9 protein. In yet other embodiments, at least 10% of PDX1 and NKX6.1 co-positive cells express HB9 protein. In alternate embodiments, at least 20% of PDX1 and NKX6.1 co-positive cells express HB9 protein. In other embodiments, at least 30% of PDX1 and NKX6.1 co-positive cells express HB9 protein. In alternate embodiments, at least 40% of PDX1 and NKX6.1 co-positive cells express HB9 protein. In other embodiments, at least 50% of PDX1 and NKX6.1 co-positive cells express HB9 protein. In yet other embodiments, at least 60% of PDX1 and NKX6.1 co-positive cells express HB9 protein. In alternate embodiments, at least 70% of PDX1 and NKX6.1 co-positive cells express HB9 protein. In other embodiments, at least 80% of PDX1 and NKX6.1 co-positive cells express HB9 protein. In yet other embodiments, at least 90% of PDX1 and NKX6.1 co-positive cells express HB9 protein. In alternate embodiments, at least 91%, 92%, 93%, 94%, 95%, 96%, 97%, 98%, or 99% of PDX1 and NKX6.1 co-positive cells express HB9 protein.

In some embodiments, a pancreatic endoderm lineage cell population consisting of PDX1, NKX6.1, and HB9 protein positive cells is transplanted into diabetic animals for further in vivo maturation to functional pancreatic endocrine cells. In another embodiment, the invention also encompasses insulin and NKX6.1 expressing cells prepared by the methods of the invention. In yet another embodiment, the invention encompasses a step-wise process of differentiating precursor cells such as pluripotent stem cells into cells of pancreatic endoderm lineage expressing HB9. The methods of invention include one or more of these steps. In particular, the method encompasses the step of differentiating pluripotent stem cells into cells expressing markers characteristic of definitive endoderm cells. This step may take approximately three days. These cells are then differentiated into cells expressing markers characteristic of gut tube cells by culturing the cells under appropriate conditions. In one embodiment, the cells may be cultured for approximately two days. The cells expressing markers characteristic of gut tube cells are then differentiated into cells expressing markers characteristic of foregut endoderm cells. This differentiation may be achieved by culturing the cells for approximately two days. In further embodiments, the pluripotent stem cells are human embryonic pluripotent stem cells.

These cells are then differentiated into cells expressing markers characteristic of pancreatic foregut precursor cells, which in turn may then be differentiated into cells expressing markers characteristic of pancreatic endoderm/endocrine precursor cells, which in turn may then be differentiated into cells expressing markers characteristic of pancreatic endocrine cells. To achieve differentiation into pancreatic endoderm lineage cells expressing HB9, the cells expressing markers characteristic of pancreatic foregut precursor cells, and pancreatic endoderm/endocrine precursor cells may be cultured with one or more of an activin receptor inhibitor (preferably an ALK5 inhibitor), and/or a T3/T4 thyroid hormone. In one embodiment, the cells expressing markers characteristic of pancreatic foregut precursor cells, and pancreatic endoderm/endocrine precursor cells are cultured with T3/T4. In another embodiment, the cells expressing markers characteristic of pancreatic foregut precursor cells, and pancreatic endoderm/endocrine precursor cells are cultured with an activin receptor inhibitor. In an alternate embodiment, the cells are cultured with both an activin receptor inhibitor and T3/T4. The methods of the invention are suitable for any cells that may be differentiable into cells of pancreatic endoderm lineage expressing HB9. Table III illustrates exemplary culture conditions suitable for use in embodiments of methods of the invention. As used in Table III below, "MCX" is MXC compound, "AA" is activin, "ALK5 inh." is ALK5 inhibitor, "RA" is retinoic acid, "Vit. C" is ascorbic acid, "inh." is inhibitor, and "act." is activator. In certain embodiments, any one of the treatments at one stage (e.g. any one of Stage 1, 2, 3, 4, 5 or 6) may be combined with any one of the treatments at another stage (e.g. any one of Stage 1, 2, 3, 4, 5 or 6).

TABLE III

Exemplary culture conditions suitable for use in embodiments of the methods of the invention

|  | Stage 1 | Stage 2 | Stage 3 | Stage 4 | Stage 5 | Stage 6 |
|---|---|---|---|---|---|---|
| Treatment of With at least | Pluripotent stem cells AA & Wnt3A GDF8 & MCX | Stage 1 cells FGF7 & Vit. C | Stage 2 cells SANT-1, RA & Noggin FGF7, retinoic acid, SANT-1, a PKC act.(e.g. TPB), a BMP inh. (e.g. LDN-193189), & Vit. C | Stage 3 cells | Stage 4 cells | Stage 5 cells |
| Other optional components |  |  |  | T3 T3 T3 One or more of: SANT-1 RA Vit. C FGF7 BMP Receptor Inh. (e.g. LDN-193189) PKC act. (e.g. TPB) | ALK5 inh. + T3 ALK5 inh. + T3 T3 One or more of: SANT-1 RA Vit. C | T3 ALK5 inh. + T3 T3 One or more of: SANT-1 RA Vit. C |
| Duration of Treatment | Approximately 2-5 days; preferably about 3-4 days | Approximately 2-3 days; preferably about 2 days | Approximately 2-4 days, preferably about 2 days | Approximately 2-4 days, preferably about 3 days | Approximately 2-4 days, preferably about 3 days | Approximately 2-4 days, preferably about 3 days |

In an embodiment, the present invention provides a method of enhancing expression of HB9 by culturing a population of pancreatic endoderm lineage cells in media comprising T3. In some embodiments, the population of pancreatic endoderm lineage cells does not substantially express CDX2 or SOX2. In other embodiments, the population of pancreatic endoderm lineage cells is obtained by a stepwise differentiation of pluripotent cells. In additional embodiments, the pluripotent cells are human embryonic pluripotent cells.

In an embodiment, the present invention provides a method of enhancing expression of HB9 by culturing a population of pancreatic endoderm lineage cells in a medium comprising ALK5 inhibitor. In some embodiments, the population of pancreatic endoderm lineage cells is obtained by a stepwise differentiation of pluripotent cells. In some embodiments, the pluripotent cells are human embryonic pluripotent cells.

In a preferred embodiment, the present invention relates to a method of enhancing expression of HB9 by culturing a population of pancreatic endoderm lineage cells in a medium comprising an ALK5 inhibitor and T3. In some embodiments, the population of pancreatic endoderm lineage cells is obtained by a stepwise differentiation of pluripotent cells. In additional embodiments, the pluripotent cells are human embryonic pluripotent cells.

In another embodiment, the invention refers to a method of enhancing expression of HB9 in PDX1 and NKX6.1 co-expressing cells by treating such cells in a medium comprising a sufficient amount of T3, ALK5 inhibitor or combinations thereof.

One embodiment of the invention is a method for producing cells expressing markers characteristic of β cells from pluripotent stem cells, including the steps of: (a) culturing pluripotent stem cells; (b) differentiating the pluripotent stem cells into cells expressing markers characteristic of foregut endoderm cells; and (c) differentiating the cells expressing markers characteristic of foregut endoderm cells into cells expressing markers characteristic of β cells by treatment with a medium supplemented with T3/T4, an ALK5 inhibitor, or both. The resulting cells may be positive for NKX6.1, PDX1, and Hb-9. The method may be used to enhance the number of HB9 positive cells in NKX6.1 positive cells expressing markers characteristic of pancreatic endoderm precursor cells. The method may also be used to decrease expression of NKX2.2. Moreover, the method suppresses SOX2 and albumin expression. Further, the method may be used to increase the yield of cells expressing insulin.

In one embodiment, T3 is used. The method may include culturing cells in a medium supplemented with T3 and an ALK5 inhibitor. The method may also enhance HB9 expression when compared to cells that are not cultured with a medium supplemented with T3 and an ALK5 inhibitor. The medium may also be further supplemented with any one or more (e.g. 1, 2, 3 or all) of a SMO inhibitor, a SHH signaling pathway antagonist (such as SANT-1), retinoic acid, and ascorbic acid. In one embodiment, the method provides cells expressing markers characteristic of β cells by culturing cells expressing markers characteristic of pancreatic endoderm/endocrine precursor cells in a medium supplemented with T3, which may also be further supplemented with an ALK5 inhibitor.

Another embodiment of the invention is a method of providing cells expressing markers characteristic of β cells including differentiating cells expressing markers characteristic of foregut endoderm cells into cells expressing markers characteristic of β cells by treatment with a medium supplemented with T3/T4, an ALK5 inhibitor, or both. In certain embodiments, the medium is further supplemented with a BMP receptor inhibitor and a PKC activator. The resulting cells are preferably positive for NKX6.1, PDX1, and Hb-9. The method may be used to enhance the number of HB9 positive cells in NKX6.1 positive pancreatic endoderm precursor cells, decrease expression of NKX2.2, and/or suppresses SOX2 and albumin expression. In preferred embodiments, T3 is used. The method may also include culturing cells in a medium supplemented with T3 and an ALK5 inhibitor. The method may also enhance HB9 expression when compared to cells that are not cultured with a medium supplemented with T3 and an ALK5 inhibitor. Moreover, the method may include formation of cells expressing markers characteristic of β cells by culturing cells expressing markers characteristic of pancreatic endoderm/endocrine precursor cells in a medium supplemented with T3 and optionally an ALK5 inhibitor.

Yet another embodiment of the invention is a method of increasing HB9 expression and suppressing SOX2 and albumin expression by culturing cells expressing markers characteristic of pancreatic foregut precursor cells in a medium supplemented with T3/T4 and an ALK5 inhibitor. An alternate embodiment of the invention is a method of downregulating glucagon, somatostatin and ghrelin in cells expressing markers characteristic of pancreatic foregut precursor cells, cells expressing markers characteristic of pancreatic endoderm/endocrine precursor cells, or cells expressing markers characteristic of endocrine cells, comprising culturing the cells in a medium supplemented with T3/T4 and an ALK5 inhibitor. The medium may be further supplemented with one or more of a SMO inhibitor, a SHH signaling pathway antagonist (such as SANT-1), retinoic acid, and ascorbic acid. In one embodiment, the cells are Stage 4 cells and the medium is further supplemented with FGF7.

The invention also provides a cell or population of cells obtainable by a method of the invention. The invention also provides a cell or population of cells obtained by a method of the invention.

The invention provides methods of treatment. In particular, the invention provides methods for treating a patient suffering from, or at risk of developing, diabetes.

The invention also provides a cell or population of cells obtainable or obtained by a method of the invention for use in a method of treatment. In particular, the invention provides a cell or population of cells obtainable or obtained by a method of the invention for use in a method of treating a patient suffering from, or at risk of developing, diabetes.

The diabetes may be Type 1 or Type 2 diabetes.

In one embodiment, the method of treatment comprises implanting cells obtained or obtainable by a method of the invention into a patient.

In one embodiment, the method of treatment comprises
    differentiating pluripotent stem cells in vitro into Stage 1, Stage 2, Stage 3, Stage 4, Stage 5 or Stage 6 cells, for example as described herein,
    and implanting the differentiated cells into a patient.

In one embodiment, the method further comprises the step of culturing pluripotent stem cells, for example as described herein, prior to the step of differentiating the pluripotent stem cells.

In one embodiment, the method further comprises the step of differentiating the cells in vivo, after the step of implantation.

In one embodiment, the patient is a mammal, preferably a human.

In one embodiment, the cells may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells in vivo, additional factors, such as growth factors, antioxidants or anti-inflammatory agents, can be administered before, simultaneously with, or after the administration of the cells. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one embodiment, the method of treatment further comprises incorporating the cells into a three-dimensional support prior to implantation. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Publications cited throughout this document are hereby incorporated by reference in their entirety. The present invention is further illustrated, but not limited, by the following examples.

EXAMPLES

Example 1

Previously Published Protocols Generating Pancreatic Endoderm Population Derived from Human Pluripotent Cells do not Substantially Express HB9 Protein This example is directed to identification of the expression pattern of HB9 in cells derived from pluripotent stem cells as described in this Example. Cells of the human embryonic stem cell line H1 (passage 40) were seeded as single cells at $1\times10^5$ cells/cm$^2$ on MATRIGEL™ (1:30 dilution; BD Biosciences, NJ)-coated dishes in MTESR®1 media (StemCell Technologies, Vancouver, Canada) supplemented with 10 µM of Y27632 (Rock inhibitor, Catalog No. Y0503, Sigma-Aldrich, St. Louis, Mo.). Forty-eight hours post seeding, the cultures were washed with incomplete PBS (phosphate buffered saline without Mg or Ca). The cultures were then differentiated into pancreatic endoderm/endocrine precursor cells as described previously in *Diabetes*, 61, 2016, 2012. The differentiation protocol used was as follows:
  a. 60-70% confluent adherent cultures of undifferentiated H1 cells plated on 1:30 MATRIGEL™ coated surfaces were exposed to RPMI 1640 medium (Invitrogen) supplemented with 0.2% fetal bovine serum (FBS) (Hyclone, Utah), 100 ng/ml activin-A (AA; Pepro-tech; Rocky Hill, N.J.), and 20 ng/ml of Wnt3A (R&D Systems) for day one only. For the next two days, the cells were cultured in RPMI with 0.5% FBS and 100 ng/ml AA.
  b. The cells resulting from (a) were exposed to DMEM-F12 medium (Invitrogen) supplemented with 2% FBS and 50 ng/ml of FGF7 (Pepro-tech) for three days.
  c. The cultures resulting from (b) were continued for four days in DMEM-HG medium (Invitrogen) supplemented with 0.25 µM SANT-1 (Sigma-Aldrich; St. Louis, Mo.), 2 µM retinoic acid (Sigma-Aldrich), 100 ng/ml of Noggin (R&D Systems), and 1% (v/v) of a supplement sold under the trademark B27® (Catalogue #17504044, Life Technologies Corporation, Grand Island, N.Y.).
  d. Cells resulting from (c) were cultured for three days in DMEM-HG medium supplemented with 1 µM ALK5 inhibitor (ALK5i; Farmingdale, N.Y.), 100 ng/mL of Noggin, 50 nM TPB ((2S,5S)-(E,E)-8-(5-(4-(Trifluoromethyl)phenyl)-2,4-pentadienoylamino)benzolactam; EMD Chemicals Inc., Gibbstown N.J.) and 1% B27 in monolayer format. For the last day of culture, cells were treated with 5 mg/mL Dispase for 5 min, followed by gentle pipetting to mix and break into cell clumps (<100 micron). The cell clusters were transferred into disposable polystyrene 125 ml Spinner Flask (Corning), and spun at 80 to 100 rpm overnight in suspension with DMEM-HG supplemented with 1 µM ALK5 inhibitor, 100 ng/ml of Noggin and 1% B27.

At the end of (d), mRNA was collected for PCR analysis of relevant pancreatic endoderm/endocrine genes. Total RNA was extracted with the RNeasy® Mini Kit (Qiagen; Valencia, Calif.) and reverse-transcribed using a High Capacity cDNA Reverse Transcription Kit (Applied Biosystems, Foster City, Calif.) according to the manufacturer's instructions. cDNA was amplified using Taqman® Universal Master Mix and Taqman® Gene Expression Assays which were pre-loaded onto custom Taqman® Arrays (Applied Biosystems). The data were analyzed using Sequence Detection Software (Applied Biosystems) and normalized to undifferentiated human embryonic stem (hES) cells using the ΔΔCt method (i.e. qPCR results corrected with internal controls ($\Delta\Delta Ct = \Delta Ct_{sample} - \Delta Ct_{reference}$)). All primers were purchased from Applied Biosystems. FACS and immunofluorescent analysis was done as previously described (*Diabetes*, 61, 20126, 2012). The HB9 antibody was obtained from Developmental Studies Hybridoma Bank (University of Iowa, Iowa). As used in the Examples, Y27632 ((1R,4r)-4-((R)-1-aminoethyl)-N-(pyridin-4-yl)cyclohexanecarboxamide) is a cell-permeable small molecule Rho-associated kinase (ROCK) inhibitor.

Figure 1B:
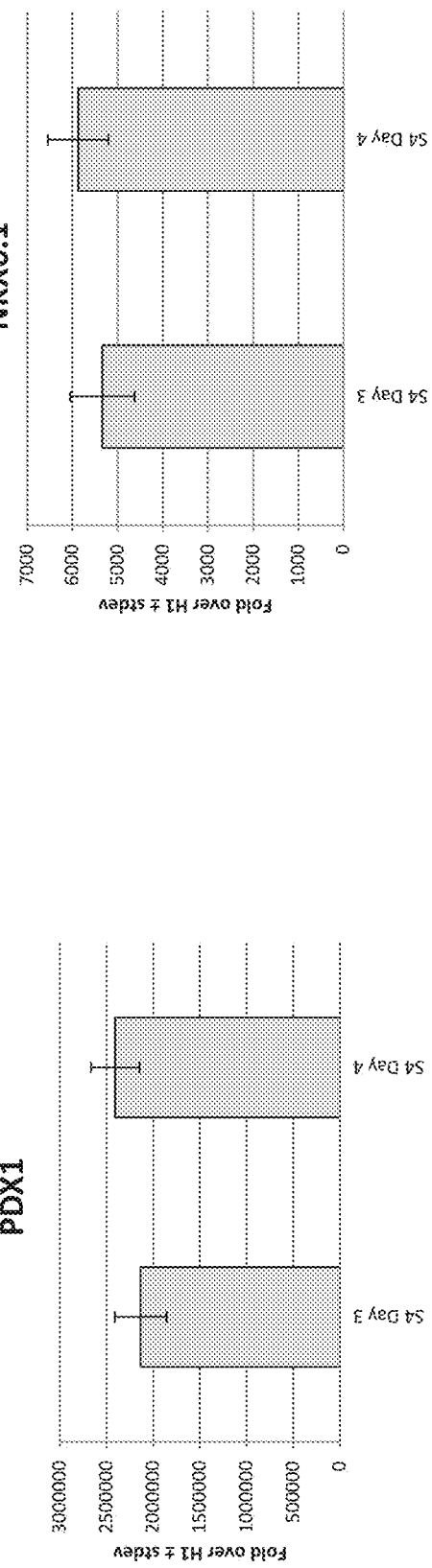
Figure 1C:
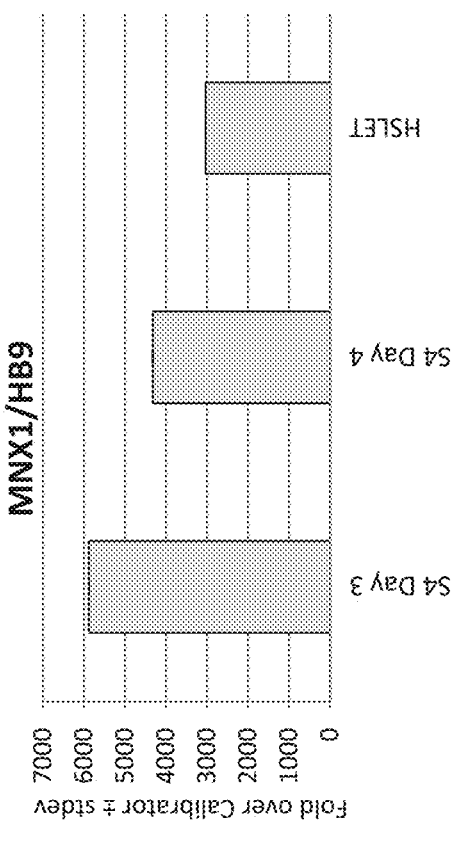
Figures 2A, 2B, 2C:
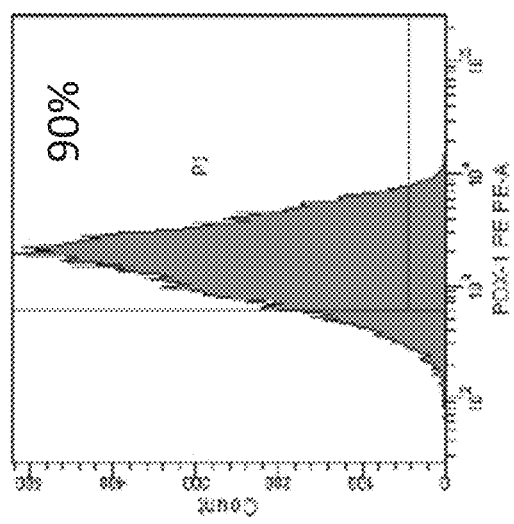
FIGS. 2A to 2C show the results of FACS analysis of the human embryonic stem cell line H1 differentiated to pancreatic endoderm/endocrine precursors as outlined in Example 1 for PDX1 (FIG. 2A), NKX6.1 (FIG. 2B) and HB9 (FIG. 2C).

FIGS. 1A to 1C depict data from real-time PCR analyses of the expression of the following genes in cells of the human embryonic stem cell line H1 differentiated to pancreatic endoderm/endocrine precursors as outlined in Example 1: PDX1 (FIG. 1A), NKX6.1 (FIG. 1B), and HB9 (FIG. 1C). As shown in FIGS. 1A-1C, robust mRNA expression of PDX1, NKX6.1, and HB9 was detected in these cultures. Furthermore, mRNA expression of HB9 was equivalent or higher in these cells as compared to human cadaveric islets. However, as shown in FIGS. 2A-2C, whereas gene expression data for PDX1 and NKX6.1 was in accordance with high expression of the corresponding proteins as measured by FACS analysis, mRNA expression of HB9 was discordant with protein expression of HB9. On the day following the completion of (d), i.e., at day 5, approximately 1% of the cells were positive for HB9 whereas approximately 50% of the cells were NKX6.1 positive and approximately 90% were PDX1 positive. Immunostaining of the cell clusters also confirmed the FACS data. As shown in FIGS. 3A-3B, a significant number of NKX6.1 positive cells and few insulin positive cells were present in the clusters. However, there were no HB9 positive cells detected by immunostaining (FIG. 3B).

Example 2

Addition of T3 at Stage 4 to Stage 6 Enhances the Number of HB9 Positive Cells

This example is directed to the addition of T3 at Stage 4 to Stage 6 to significantly enhance the number of HB9 positive cells.

Cells of the human embryonic stem cell line H1 (passage 40) were seeded as single cells at $1\times10^5$ cells/cm$^2$ on MATRIGEL™ (1:30 dilution; BD Biosciences, NJ)-coated dishes in mTeSR®1 media supplemented with 10 µM of Y27632. Forty-eight hours post-seeding, cultures were washed with incomplete PBS (phosphate buffered saline without Mg or Ca). Cultures were differentiated into cells expressing markers characteristic of pancreatic endoderm/endocrine precursor cells by the protocol outlined below.

a. Stage 1 (3 days): The stem cells were cultured for one day in: MCDB-131 medium (Invitrogen Catalog No. 10372-019) supplemented with 2% fatty acid-free BSA (Proliant Catalog No. 68700), 0.0012 g/ml sodium bicarbonate (Sigma-Aldrich Catalog No. S3187), 1× GlutaMax™ (Invitrogen Catalog No. 35050-079), 4.5 mM D-glucose (Sigma-Aldrich Catalog No. G8769), 100 ng/ml GDF8 (R&D Systems) and 1 µM of the MCX Compound. The cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.

b. Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).

c. Stage 3 (2 days): The Stage 2 cells were then treated with MCDB-131 medium supplemented with a 1:200 dilution of ITS-X (Gibco® Insulin,-Transferrin-Selenium-Ethanolamine; Invitrogen, Ca); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN (BMP receptor inhibitor; Catalog No. 04-0019; Stemgent) for two days.

d. Stage 4 (3 days): The Stage 3 cells were then treated with MCDB-131 medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; and 100 nM TPB for three days.

e. Stage 5 (3 days): The Stage 4 cells were then treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.25 mM ascorbic acid; and 500 nM of ALK5 inhibitor SD208 for three days. SD208 is 2-(5-Chloro-2-fluorophenyl)pteridin-4-yl]pyridin-4-yl-amine) having the structure of formula I, and disclosed in Molecular Pharmacology 2007, 72:152-161. SD208 is a 2,4-disubstituted pteridine, ATP-competitive inhibitor of the TGF-βR I kinase.

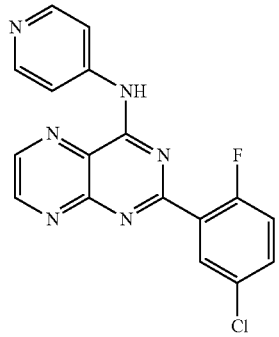

(I)

f. Stage 6 (3-15 days): The Stage 5 cells were treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.25 mM ascorbic acid for three days.

In some cultures, 1 µM T3 (T6397, Sigma, MO) was added at Stages 4 through 6. At the end of Stages 4 through 6, the control and treated cultures were analyzed by FACS and immunostaining. Furthermore, mRNA was collected for the control and treated cultures at Stages 2 through 6.

Figure 5A:
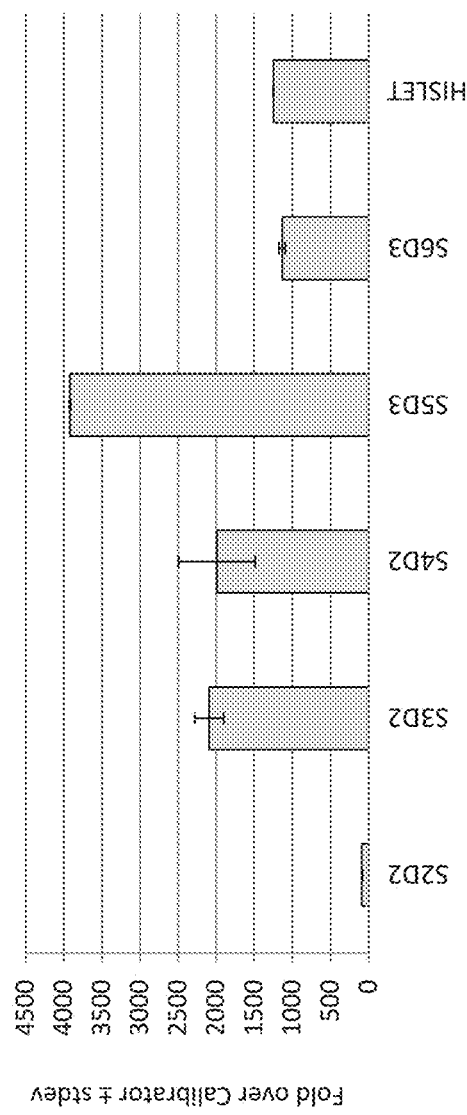
FIGS. 5A-5B are a bar graph and two digital images.
Figure 5B:
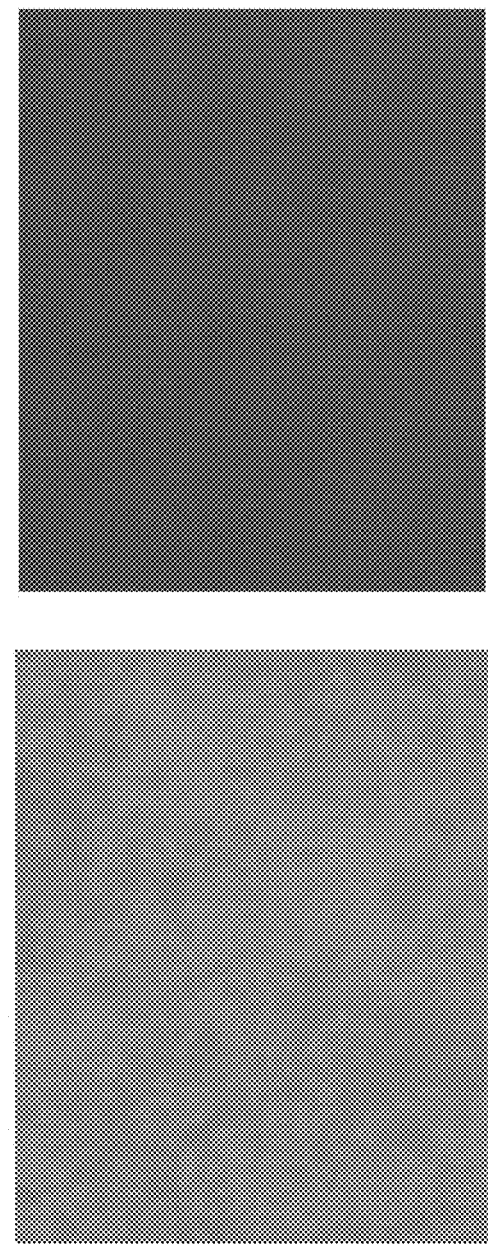

FIGS. 4A-4C depict FACS data at Stage 4 (FIG. 4A), Stage 5 (FIG. 4B), and Stage 6 (FIG. 4C) for PDX1, NKX6.1, and HB9. Consistent with data from Example 1, although there were substantial numbers of PDX1 and NKX6.1 positive cells at Stages 4 through 6, expression of HB9 was far lower. Expression for HB9 peaked at Stage 5 and was diminished at Stage 6. Overall, expression of HB9 for cells generated using the protocol outlined in Example 2 was higher as compared to cells generated using the protocol outlined in Example 1. FIG. 5A shows mRNA expression of HB9 as compared to human islets at Stages 2 through 6. Similar to Example 1, although the mRNA expression level of HB9 at Stages 3 to 4 was equivalent to human islets, HB9 protein expression was very low at Stage 4 (FIG. 5B).

Figure 6A:
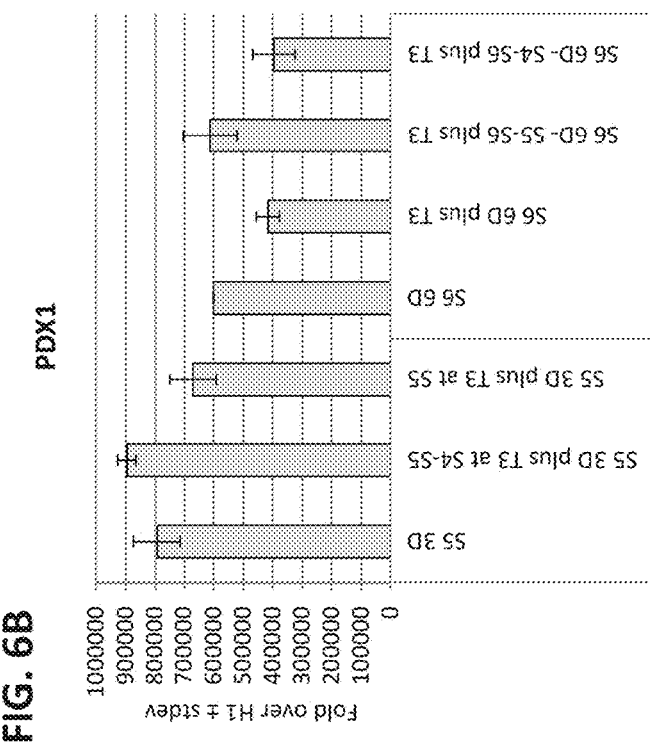
FIGS. 6A to 6J depict data from real-time PCR analyses of the expression of the following genes in cells of the human embryonic stem cell line H1 differentiated to Stage 4 as outlined in Example 2 and then treated at Stage 4 only, Stage 4 through Stage 5, or Stage 4 through Stage 6.
Figure 6B:
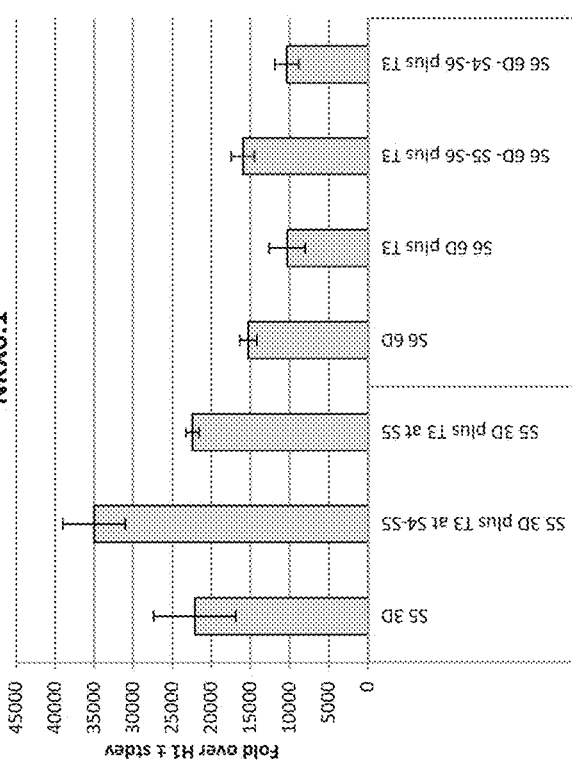
Figure 6C:
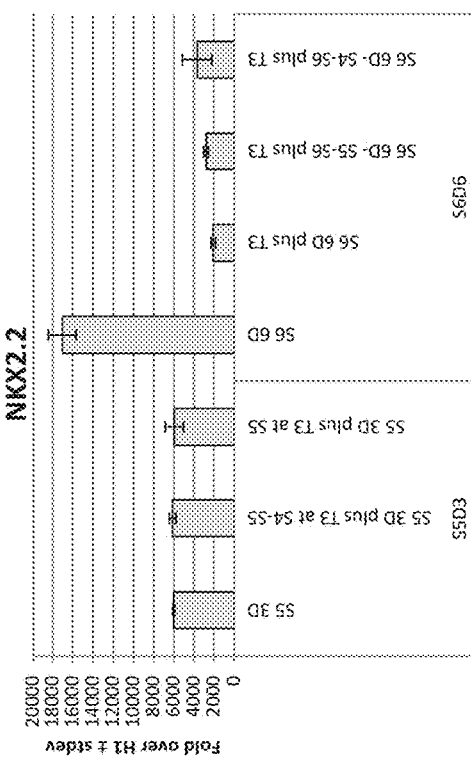
Figure 6E:
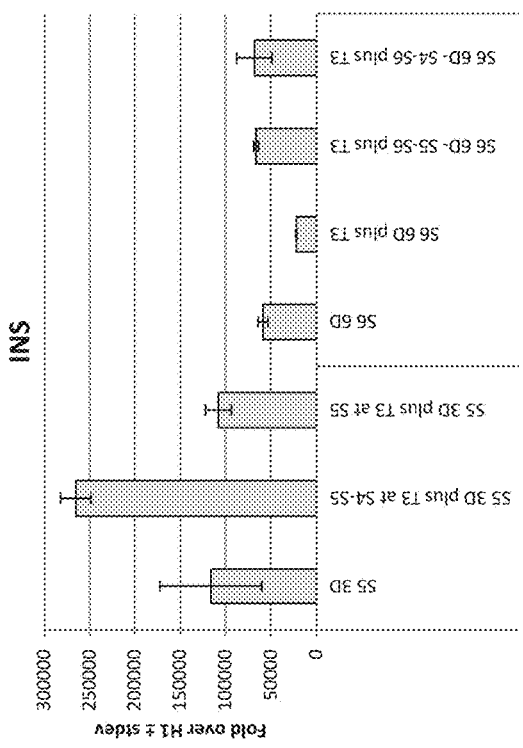
Figure 6D:
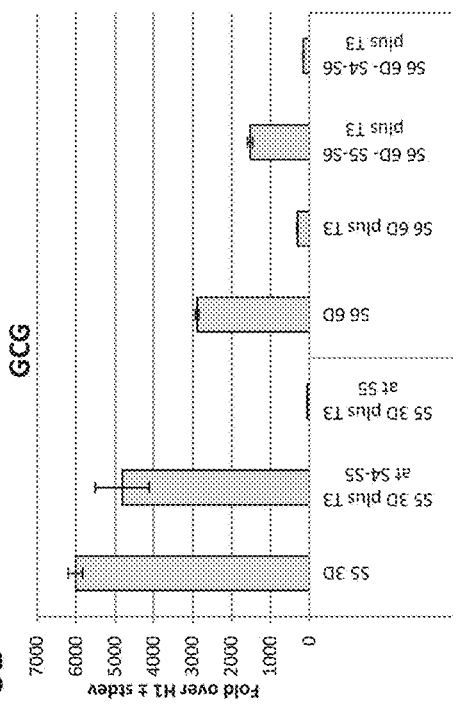
Figure 6F:
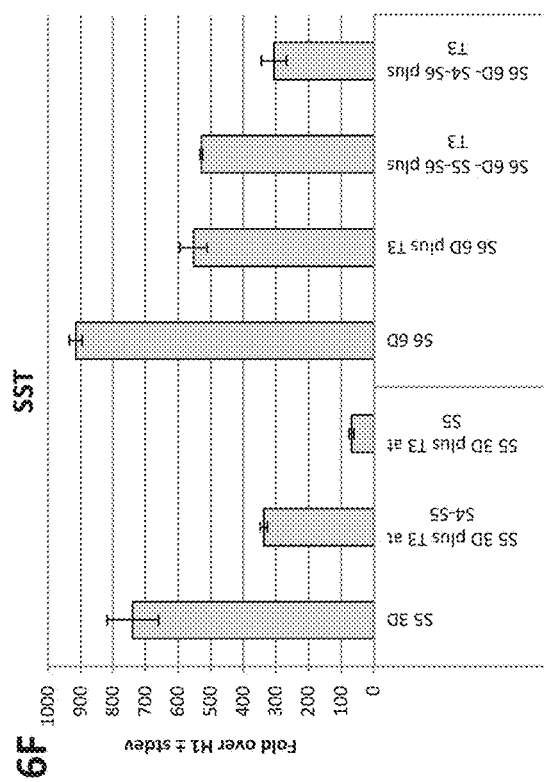
Figure 6H:
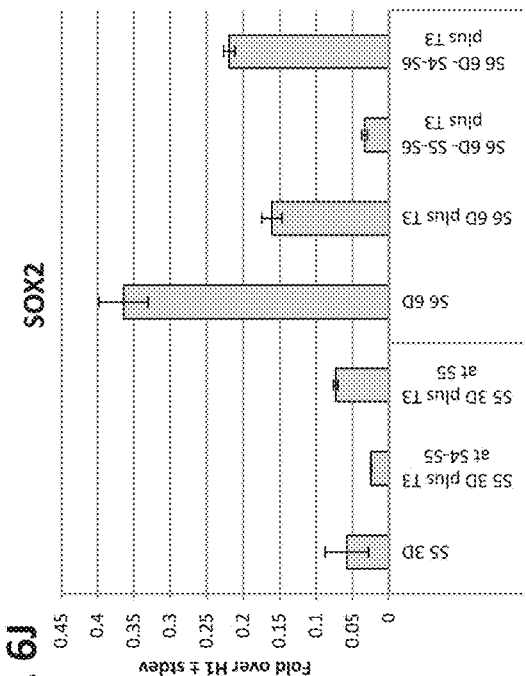
Figure 6G:
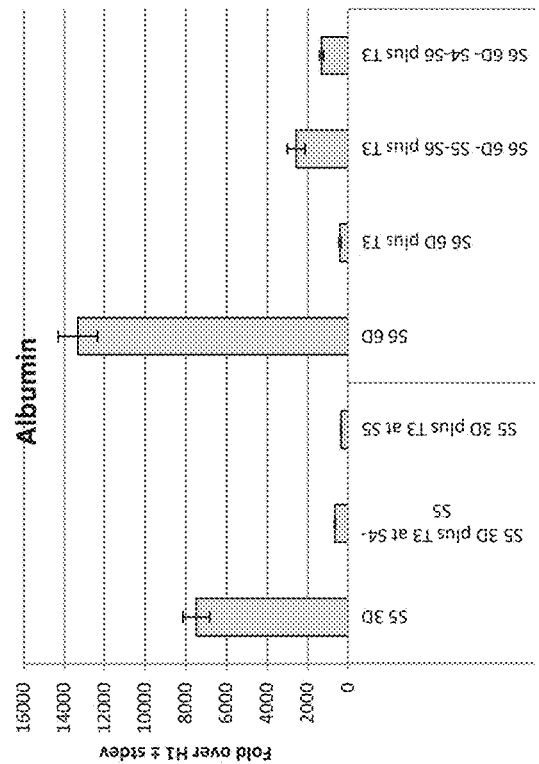
Figure 6J:
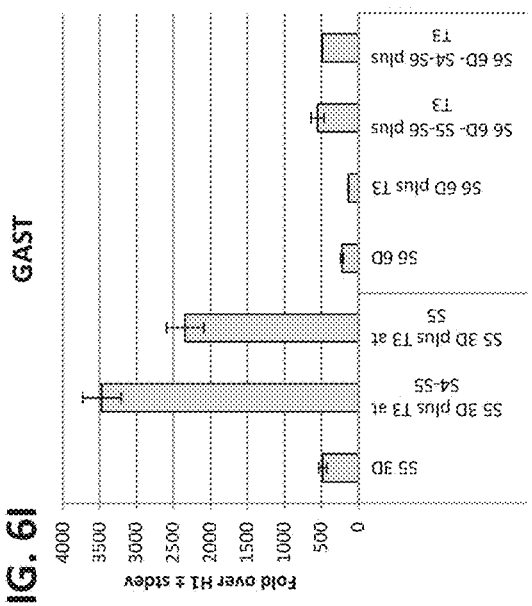
Figure 6I:
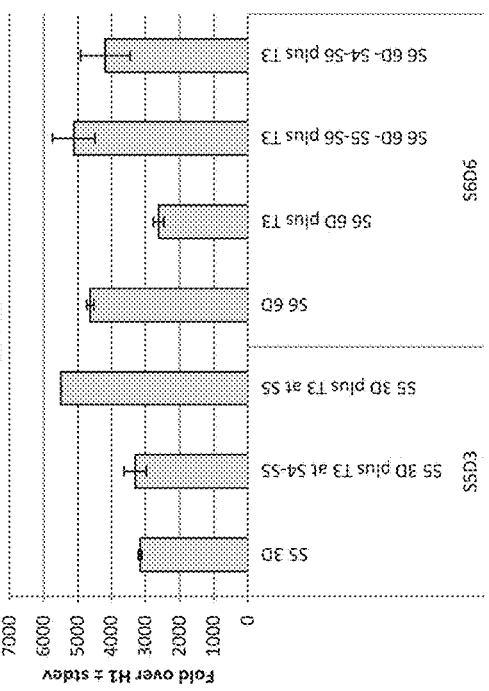

FIGS. 6A to 6J depict data from real-time PCR analyses of the expression of the following genes in cells of the human embryonic stem cell line H1 differentiated to Stage 4 as outlined in Example 2 and treated at Stage 4 only, Stage 4 through Stage 5, or Stage 4 through Stage 6: NKX6.1 (FIG. 6A); PDX1 (FIG. 6B); NKX2.2 (FIG. 6C); glucagon (FIG. 6D); insulin (FIG. 6E); somatostatin (FIG. 6F); CDX2 (FIG. 6G); albumin (FIG. 6H); gastrin (FIG. 6I); and SOX2 (FIG. 6J). The addition of T3 at Stages 4 through 6 significantly down regulated glucagon, somatostatin, and ghrelin while moderately increasing insulin expression at Stage 5. The addition of T3 at Stages 4 through 6 appears to have significantly decreased expression of NKX2.2, while apparently not affecting NKX6.1 and PDX1 expression. Furthermore, T3 addition suppressed SOX2 (stomach marker) and albumin (liver marker) expression while not affecting CDX2 (intestine marker) expression. Immunostaining of control and treated cultures at Stage 6 revealed a significant increase in the number of HB9 positive cells in the T3 treated group (FIG. 7B) as compared to the control (FIG. 7A) at Stage 6. Furthermore, an increased number of NKX6.1 positive cells showed expression of HB9 in T3 treated cultures.

Example 3

Combined Treatment with T3 and an ALK5 Inhibitor at Stage 6 Enhances Expression of HB9

This example demonstrates that the combination of an ALK5 inhibitor and T3 in the medium at Stage 6 appears to significantly boost expression of HB9.

Cells of the human embryonic stem cell line H1 (passage 40) were seeded as single cells at $1 \times 10^5$ cells/cm$^2$ on MATRIGEL™ (1:30 dilution; BD Biosciences, NJ)-coated dishes in mTeSR®1 media supplemented with 10 µM of Y27632. Forty-eight hours post seeding, cultures were washed with incomplete PBS (phosphate buffered saline without Mg or Ca). Cultures were differentiated into pancreatic endoderm/endocrine lineages by the protocol outlined below.

- a. Stage 1 (3 days): The cells were cultured for one day in: MCDB-131 medium (Invitrogen Catalog No. 10372-019) supplemented with 2% fatty acid-free BSA (Proliant Catalog No. 68700), 0.0012 g/ml sodium bicarbonate (Sigma-Aldrich Catalog No. S3187), 1× GlutaMax™ (Invitrogen Catalog No. 35050-079), 4.5 mM D-Glucose (Sigma-Aldrich Catalog No. G8769), 100 ng/ml GDF8 (R&D Systems) and 1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.
- b. Stage 2 (2 days): The Stage 1 cells were treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).
- c. Stage 3 (2 days): The Stage 2 cells were treated with MCDB-131 medium supplemented with a 1:200 dilution of ITS-X (Invitrogen, Ca); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN (BMP receptor inhibitor; Catalog No. 04-0019; Stemgent) for two days.
- d. Stage 4 (3 days): The Stage 3 cells were treated with MCDB-131 medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; 100 nM TPB, and 1 µM T3 for three days.
- e. Stage 5 (3 days): The Stage 4 cells were treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.25 mM ascorbic acid; 1 µM ALK5 inhibitor SD208, and 100 nM T3 for three days.
- f. Stage 6 (3-15 days): The Stage 5 cells were treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 500 nM ALK5 inhibitor, 50 nM RA; 0.25 mM ascorbic acid and 10 nM T3 for three days.

Figure 8A:
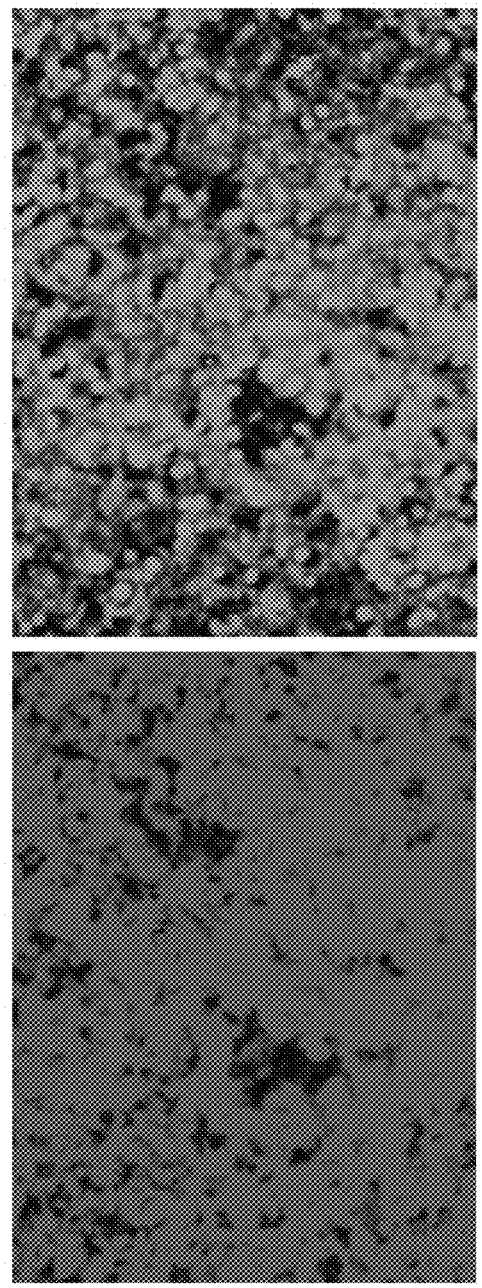
FIGS. 8A and 8B depict immunostaining for NKX6.1 and HB9 at Stage 6 day 7 for cells differentiated to Stage 6 as outlined in Example 3.
Figure 8B:
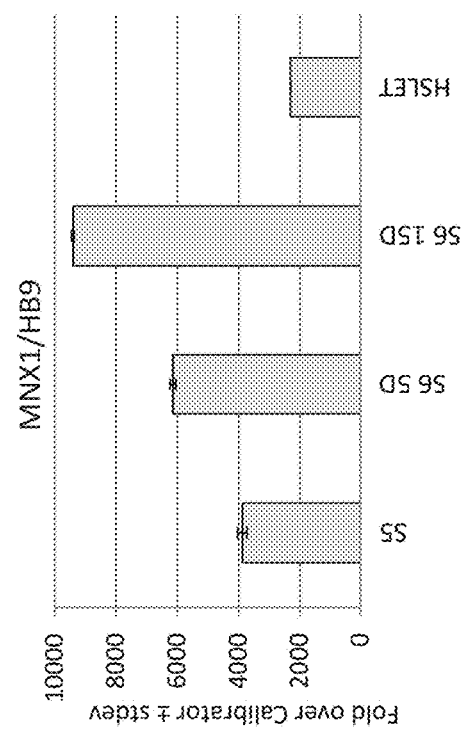
Figures 10C, 10D:
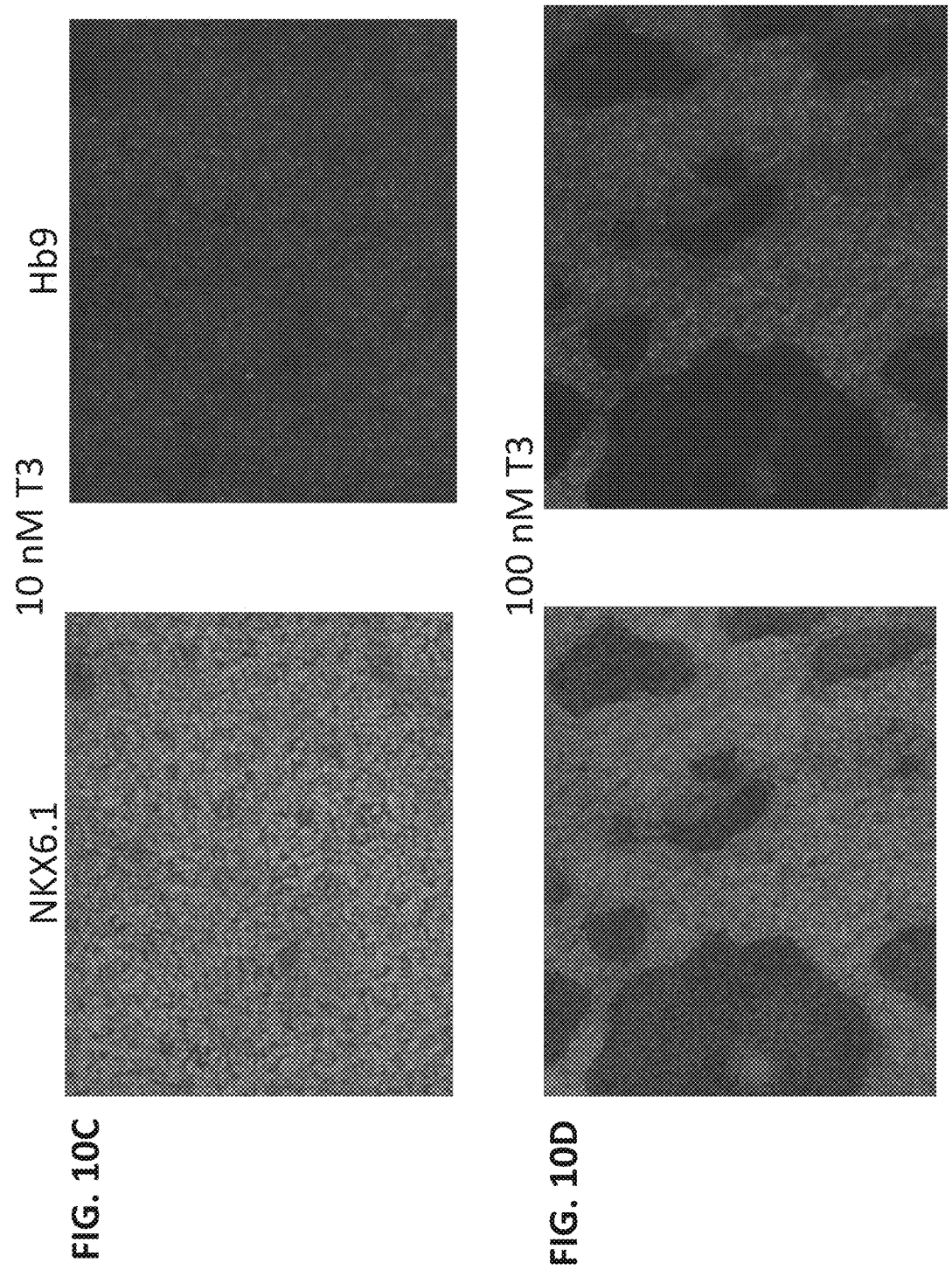
Figure 10E:
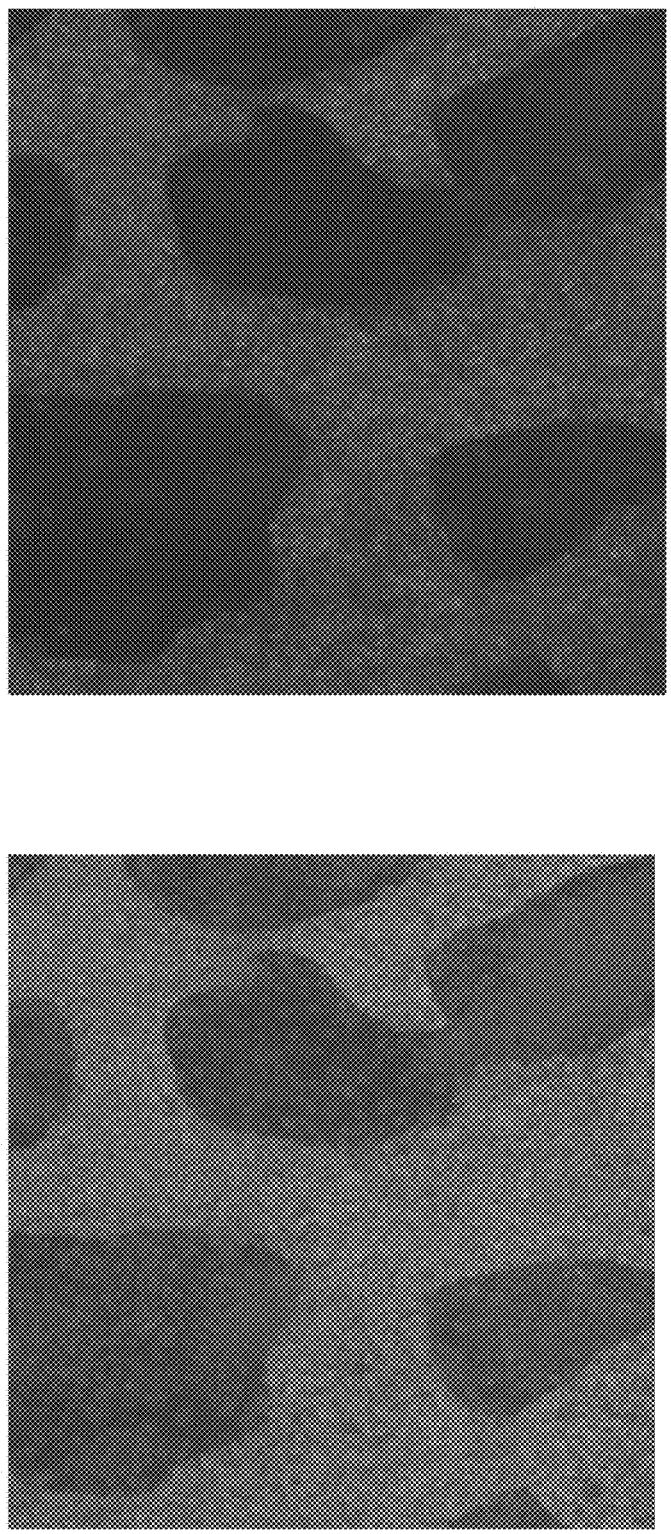

FIGS. 8A and 8B depict immunostaining for NKX6.1 and HB9 at Stage 6 day 7. FIG. 8C depicts data from real-time PCR analyses of the expression of the HB9 in cells of the human embryonic stem cell line H1 differentiated to Stage 6 as outlined in Example 3. The mRNA expression of HB9 along with the immune staining images shows that prolonged exposure to ALK5 inhibitor and T3 appear to significantly enhance expression of HB9 while maintaining robust expression of NKX6.1. FIGS. 9A and 9B depict the FACS data at Stage 6 day 5 and day 15, respectively. A significant fraction of Stage 6 cells show expression of HB9 in Stage 6 day 15 cultures.

Example 4

T3 in a Dose Dependent Manner Enhances Expression of HB9

This example shows that T3 in a dose-dependent manner may be used to enhance expression of HB9 while maintaining expression of NKX6.1 at Stage 6. Cells of the human embryonic stem cell line H1 (passage 40) were seeded as single cells at $1 \times 10^5$ cells/cm$^2$ on MATRIGEL™ (1:30 dilution; BD Biosciences, NJ)-coated dishes in mTeSR®1 media supplemented with 10 µM of Y27632. Forty-eight hours post-seeding, cultures were washed in incomplete PBS (phosphate buffered saline without Mg or Ca). Cultures were differentiated into cells expressing markers characteristic of pancreatic endoderm/endocrine precursor cells by the protocol outlined below.

- a. Stage 1 (3 days): The cells were cultured for one day in: MCDB-131 medium (Invitrogen Catalog No. 10372-019) supplemented with 2% fatty acid-free BSA (Proliant Catalog No. 68700), 0.0012 g/ml sodium bicarbonate (Sigma-Aldrich Catalog No. S3187), 1× GlutaMax™ (Invitrogen Catalog No. 35050-079), 4.5 mM D-glucose (Sigma-Aldrich Catalog No. G8769), 100 ng/ml GDF8 (R&D Systems) and 1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, 100 ng/ml GDF8, and 0.1 µM MCX compound. The cells were then cultured for an additional day in MCDB-131 medium supplemented with 2% fatty acid-free BSA, 0.0012 g/ml sodium bicarbonate, 1× GlutaMax™, 4.5 mM D-glucose, and 100 ng/ml GDF8.
- b. Stage 2 (2 days): The Stage 1 cells were then treated for two days with MCDB-131 medium supplemented with 2% fatty acid-free BSA; 0.0012 g/ml sodium bicarbonate; 1× GlutaMax™; 4.5 mM D-glucose; 0.25 mM ascorbic acid (Sigma, MO) and 25 ng/ml FGF7 (R & D Systems, MN).
- c. Stage 3 (2 days): The Stage 2 cells were then treated with MCDB-131 medium supplemented with a 1:200 dilution of ITS-X (Invitrogen, Ca); 4.5 mM glucose; 1× GlutaMax™; 0.0017 g/ml sodium bicarbonate; 2% fatty acid-free BSA; 0.25 µM SANT-1 (Sigma, MO); 1 µM RA (Sigma, MO); 25 ng/ml FGF7; 0.25 mM ascorbic acid; 200 nM TPB (PKC activator; Catalog No. 565740; EMD Chemicals, Gibbstown, N.J.); and 100 nM LDN (BMP receptor inhibitor; Catalog No. 04-0019; Stemgent) for two days.

d. Stage 4 (3 days): The Stage 3 cells were then treated with MCDB-131 medium supplemented with a 1:200 dilution of ITS-X; 4.5 mM glucose; 1× GlutaMax™; 0.0017 g/ml sodium bicarbonate; 2% fatty acid-free BSA; 0.25 µM SANT-1; 100 nM RA; 2 ng/ml FGF7; 100 nM LDN-193189; 0.25 mM ascorbic acid; 100 nM TPB for three days.

e. Stage 5 (3 days): The Stage 4 cells were then treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 50 nM RA; 0.25 mM ascorbic acid; 1 µM ALK5 inhibitor SD208, and 0-1000 nM T3 for three days.

f. Stage 6 (6 days): The Stage 5 cells were then treated with MCDB-131 medium supplemented with a 1:200 dilution of ITS-X; 4.5 mM glucose; 1× GlutaMax™; 0.0015 g/ml sodium bicarbonate; 2% fatty acid-free BSA; 0.25 µM SANT-1; 500 nM ALK5 inhibitor; 50 nM RA; 0.25 mM ascorbic acid and 0-1000 nM T3 for six days.

FIGS. 10A to 10E depict immunostaining for NKX6.1 and HB9 at Stage 6 day 6. T3 in a dose dependent manner significantly enhanced the number of HB9 positive cells in the NKX6.1 positive pancreatic endoderm precursor cells.

Figure 11E:
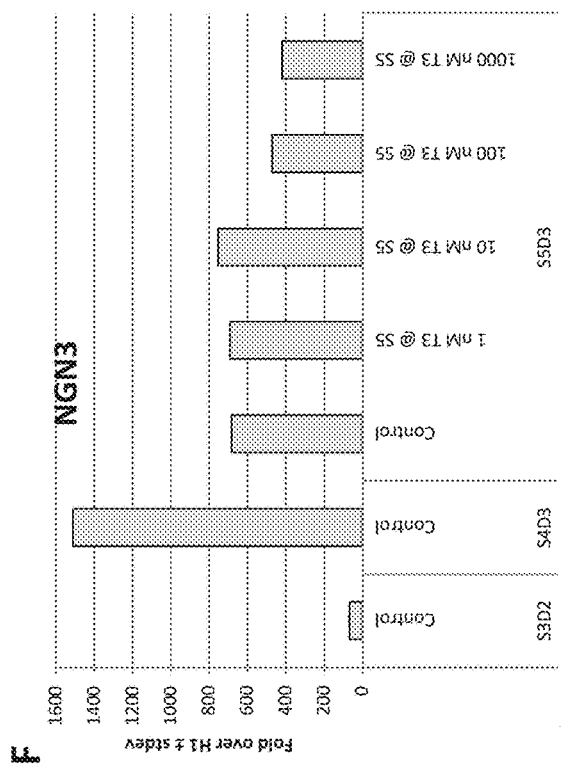
Figure 11F:
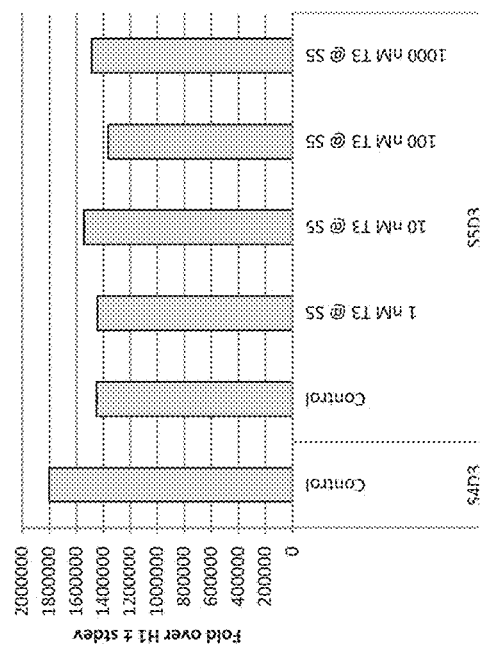
Figure 11G:
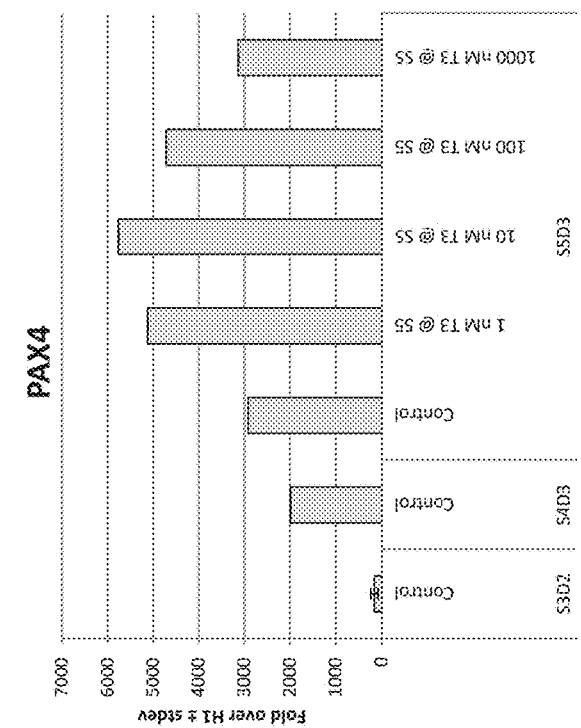
Figure 11H:
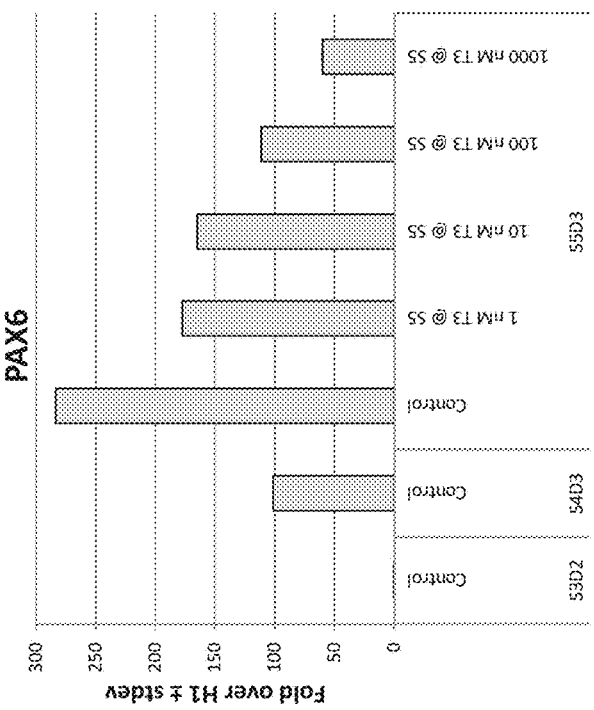
Figure 11I:
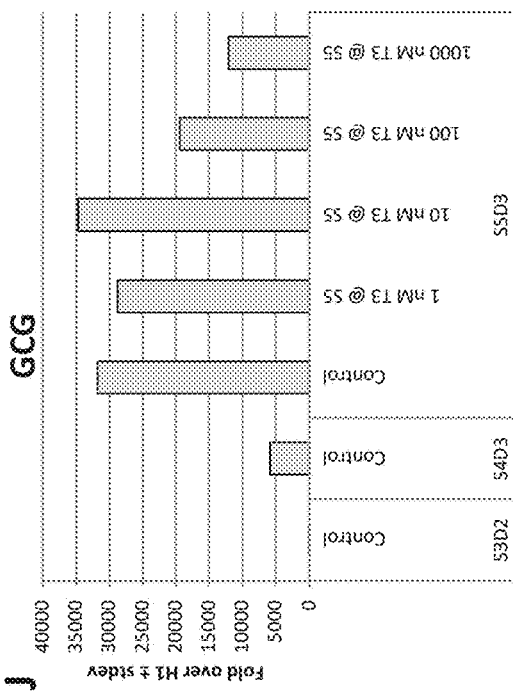
Figure 11J:
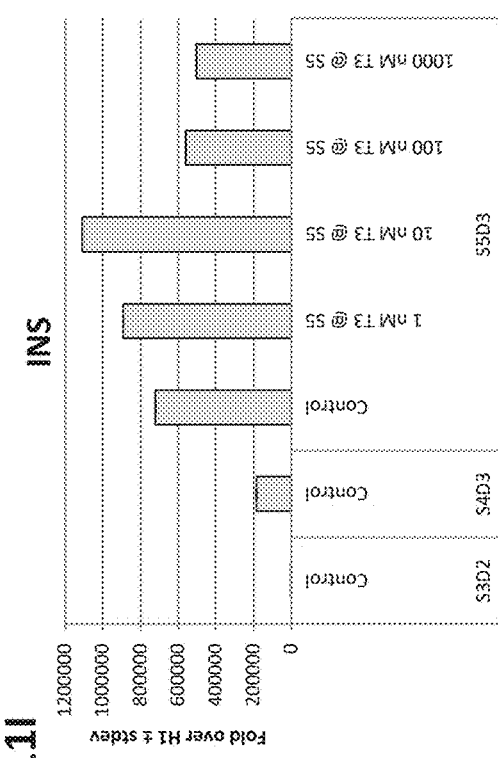
Figure 11K:
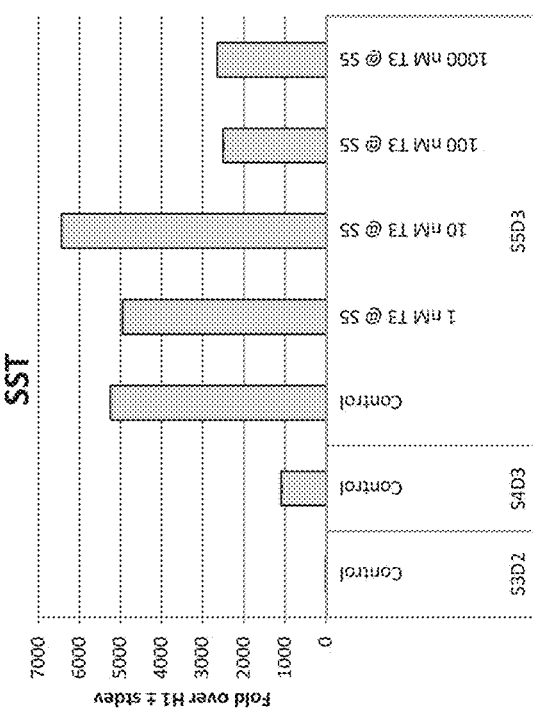
Figure 11L:
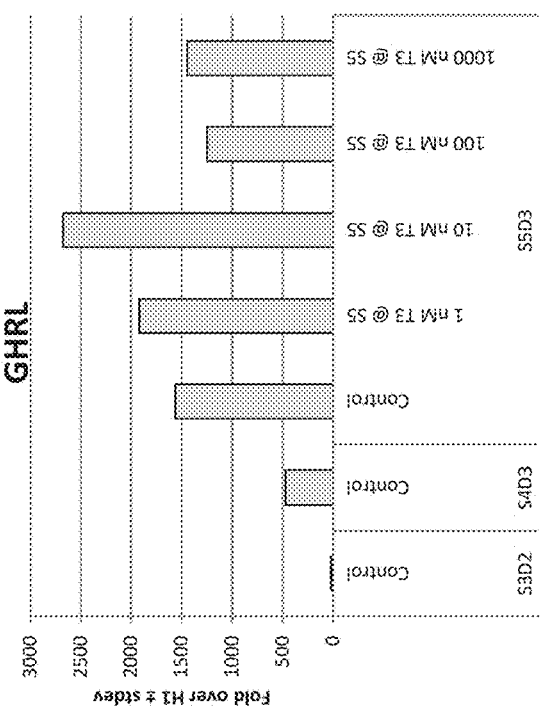

FIGS. 11A to 11L depict data from real-time PCR analyses of the expression of the following genes in cells of the human embryonic stem cell line H1 differentiated to Stage 6 as outlined in Example 4: SOX2 (FIG. 11A); NKX6.1 (FIG. 11B); NKX2.2 (FIG. 11C); gastrin (FIG. 11D); PDX1 (FIG. 11E); NGN3 (FIG. 11F); PAX6 (FIG. 11G); PAX4 (FIG. 11H); insulin (FIG. 11I); glucagon (FIG. 11J); ghrelin (FIG. 11K); and somatostatin (FIG. 11L).

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. An in vitro cell culture for differentiating cells derived from human pluripotent stem cells comprising:
   a) a culture vessel;
   b) a volume of differentiation medium; and
   c) a population of differentiated cells derived from human pluripotent stem cells wherein at least ten percent of said differentiated cells co-express PDX1, NKX6.1 and HB9, wherein said differentiation medium comprises a growth medium supplemented with a thyroid hormone selected from the group consisting of triiodothyronine, thyroxine, analogues of triiodothyronine, analogues of thyroxine and mixtures thereof, or
   both the thyroid hormone and ALK5 inhibitor.

2. The cell culture of claim 1, wherein said ALK5 inhibitor is SD208, ALK5 inhibitor II, or ALX-270-445.

3. The cell culture of claim 2, wherein said growth medium is MCDB131.

4. The cell culture of claim 1, wherein said differentiated cells comprise cells expressing pancreatic endocrine cell markers.

5. The cell culture of claim 2, wherein said growth medium is further supplemented with one or more of:
   a) a smoothened receptor inhibitor selected from MRT10 or cyclopamine;
   b) a SHH signaling pathway antagonist selected from SANT-1 or HPI-1;
   c) a BMP Receptor Inhibitor selected from LDN-193189, Noggin or Chordin;
   d) a PKC activator selected from TPB, PDBu, PMA, and ILV;
   e) a fibroblast growth factor selected from FGF7 or FGF10;
   f) retinoic acid;
   g) ascorbic acid;
   h) heparin; and
   i) zinc sulfate.

6. The cell culture of claim 5, wherein said growth medium is further supplemented with SANT-1, retinoic acid and ascorbic acid.

7. An in vitro cell culture comprising a population of differentiated human pluripotent stem cells expressing pancreatic endocrine cell markers wherein at least ten percent of said cells express HB9, PDX1 and NKX6.1.

8. The cell culture of claim 7, wherein at least thirty percent of the cells that express both NKX6.1 and PDX1 also express HB9.

9. The cell culture of claim 7, wherein at least fifty percent of the cells that express both NKX6.1 and PDX1 also express HB9.

10. The cell culture of claim 7, wherein at least eighty percent of the cells that express both NKX6.1 and PDX1 also express HB9.

11. The cell culture of claim 4, wherein said differentiated cells comprise cells expressing β cell markers.

12. The cell culture of claim 11, wherein said differentiated cells produce insulin.

* * * * *